United States Patent [19]
Toukatly et al.

[11] Patent Number: 5,698,439
[45] Date of Patent: Dec. 16, 1997

[54] NOVEL MALIGNANT CELL TYPE MARKERS OF THE INTERIOR NUCLEAR MATRIX

[75] Inventors: Gary Toukatly, Amhurst, N.H.; Graham P. Lidgard, Wellesley, Mass.

[73] Assignee: Matritech, Inc., Newton, Mass.

[21] Appl. No.: 470,950

[22] Filed: Jun. 6, 1995

Related U.S. Application Data

[62] Division of Ser. No. 195,487, Feb. 14, 1994, which is a continuation of Ser. No. 901,701, Jun. 22, 1992, abandoned.

[51] Int. Cl.$^6$ .............................. C12N 1/20; C07H 21/04; G01N 33/574; C12Q 1/68
[52] U.S. Cl. ............................. 435/252.3; 435/320.1; 435/325; 435/7.2 B; 435/6; 536/23.5; 536/23.1; 536/24.3; 536/24.31; 530/358; 530/387.9
[58] Field of Search ........................ 536/23.1, 23.5, 536/24.3, 24.31; 424/139.1, 155.1; 514/44; 435/6, 320.1, 252.3, 325

[56] References Cited

U.S. PATENT DOCUMENTS

| | | | |
|---|---|---|---|
| 4,806,463 | 2/1989 | Goodchild et al. | 435/5 |
| 4,885,236 | 12/1989 | Penman et al. | 435/5 |
| 5,098,890 | 3/1992 | Gewirtz et al. | 514/44 |
| 5,273,877 | 12/1993 | Fey et al. | 435/6 |

FOREIGN PATENT DOCUMENTS

| | | |
|---|---|---|
| WO87/03910 | 7/1987 | WIPO. |
| 91 17266 | 11/1991 | WIPO. |
| WO93/09437 | 5/1993 | WIPO. |

OTHER PUBLICATIONS

Harlow et al. (1988) "Antibodies: A Laboratory Manual," *Cold Spring Harbor Laboratory*, p. 27.
Miller et al., "Release of Nuclear Matrix Proteins During Apoptotic Cell Death", *J. Cell Biology*, 115:314A (1991) (Abstract).
Miller et al., "Detection of Nuclear Matrix Proteins in Serum From Cancer Patients", *Cancer Research*, 52(2):422–427 (1992).
Sambrook et al., "Molecular Cloning", *Cold Spring Harbor Lab Press*, p. 739 (1989).
Oeller et al., "Rev. Inhibition of Tom. Fruit Senescence by Antisense RNA", *Science*, 254:437–439 (Oct. 1991).
Compton et al., *J. of Cell Biology*, 116:No. 6, 1395–1408, (Mar. 1992).
Fey et al., *Critical Reviews*, 1:Issue 2, 127–143, (1991).
Yang et al., *J. of Cell Biology*, 116:No. 6, 1303–1317 (Mar. 1992).
Lyderson et al., *Cell*, 22:489–492, (Nov. 1980).
News Release; "Clinical Utility of Matritech'Bladder Cancer Test Reported in August Issue of Journal of Urology"; Jul. (1996).
Keesee, et al.; "Utilization of Nuclear Matrix Proteins for Cancer Diagnosis"; *Critical Reviews in Eukaryotic Gene Expression*; 6(2&3):189–214 (1996).

Todorov, et al.; "Detection of the 125–kDa Nuclear Protein Mitotin in Centrosomes, the Poles of the Mitotic Spindle, and the Midbody"; *Experiment Cell Research*; 199:398–401 (1992).
Tousson, "Centrophilin: A Novel Mitotic Spindle Protein Involved in Microtubule Nucleation"; *The J. of Cell Biology*; 112 (No. 3):427–440 (1991).
Whitfield et al.; "Cloning of a Gene Encoding an Antigen Associated with the Centrosome in Drosophila"; *J. of Cell Science*; 89:467–480 (1988).
Kallajoki et al.; "Ability to Organize Microtubules in Taxol–Treated Mitotic PtK$_2$ Cells Goes with the SPN Antigen and Not With the Centrosome"; *J. of Cell Science*; 102:91–102 (1992).
Nickerson, et al.; "A Normally Masked Nuclear Matrix Antigen That Appears at Mitosis on Cytoskeleton Filaments Adjoining Chromosomes, Centrioles, and Midbodies"; *The J. of Cell Biology*; 116 (No. 4):977–987 (Feb. 1992).
Stuurman et al.; "A Monoclonal Antibody Recognizing Nuclear Matrix–Associated Nuclear Bodies"; *J. of Cell Science*; 101:773–784 (1992).
Yang et al.; "The Nuclear–Mitotic Apparatus Protein is Important in the Establishment and Maintenance of the Bipolar Mitotic Spindle Apparatus"; *Molecular Biology of the Cell*; 3:1259–1267 (Nov. 1992).
Maekawa et al.; "Identification of a Minus End—Specific Microtubule–Associated Protein Located at the Mitotic Poles in Cultured Mammalian Cells"; *European J. of Cell Biology*; 54:255–267 (1991).
Thibodeau et al.; "Monoclonal Antibody CC–3 Recognizes Phosphoproteins in Interphase and Mitotic Cells"; *Experimental Cell Research*; 195:145–153 (1991).
Kallajoki, et al.; "A 210 kD nuclear matrix protein is a functional part of the mitotic spindle; a microinjection study using SPN monoclonal antibodies;" *EMBO J.*; 10:3351–3362 (1991).
Briggman et al.; "Detection of nuclear matrix protein in the urine of patients with transitional cell carcinoma," poster presented at NCI Conference on Chemoprevention of Premalignant and Early Malignant Lesions of the Bladder, Toas, New Mexico, Jul. 29–Aug. 2, 1992.
Compton, et al.; "Identification of Novel Centromere/Kinetochore–associated Proteins Using Monoclonal Antibodies Generated Against Human Mitotic Chromosome Scaffolds"; *The J. of Cell Biology*; 112 (No. 6):1083–1097 (Mar. 1991).

*Primary Examiner*—Lila Feisee
*Assistant Examiner*—Yvonne Eyler
*Attorney, Agent, or Firm*—Testa, Hurwitz & Thibeault, LLP

[57] ABSTRACT

Disclosed are genetic sequences and their encoded amino acid sequences for two interior nuclear matrix proteins useful as markers of malignant cell types. Primary and secondary structure analysis of the proteins is presented as well as means for their recombinant production, and compositions and methods for the use of these markers in clinical assays and cancer therapies.

9 Claims, 2 Drawing Sheets

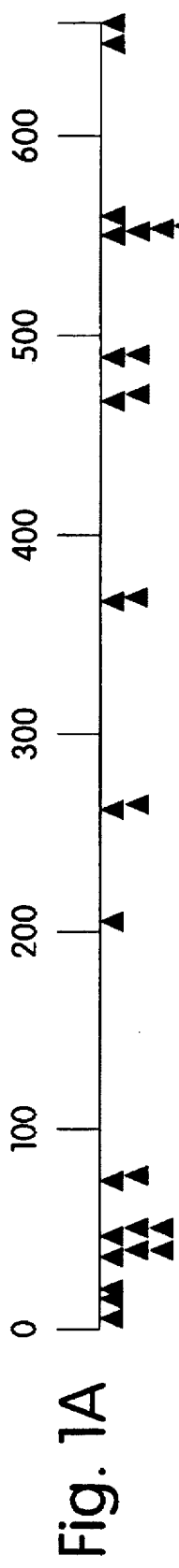
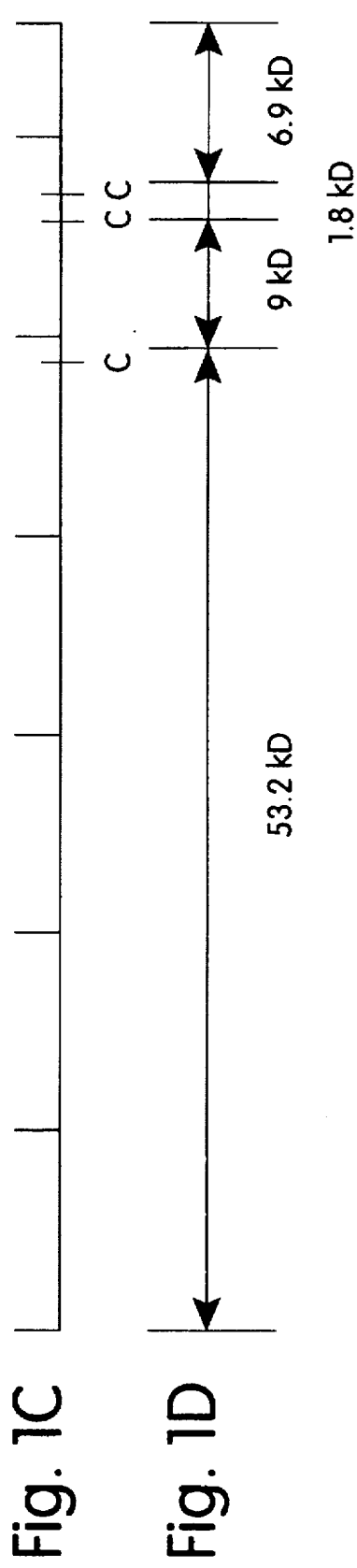
Fig. 1A  Fig. 1B  Fig. 1C  Fig. 1D

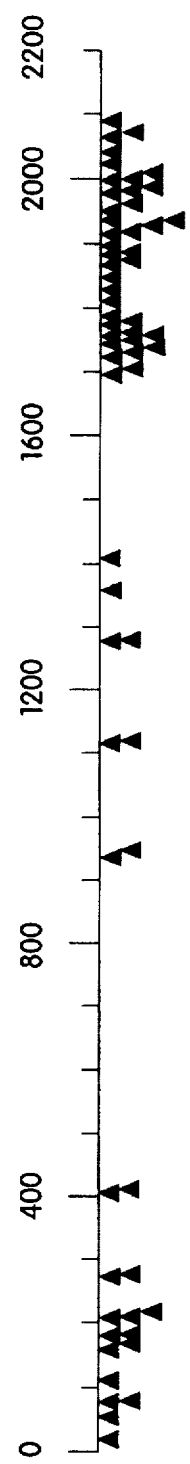
Fig. 2A
Fig. 2B

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2360 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: HOMO SAPIENS
        ( F ) TISSUE TYPE: CERVIX TUMOR ( i x ) FEATURE:
        ( A ) NAME/KEY: CDS
        ( B ) LOCATION: 94..2010

( x i ) SEQUENCE DESCRIPTION: SEQ ID NO:1:

```
GAGATGGTTC TTGGTCCTGC AGCTTATAAT GTTCCATTGC CAAAGAAATC GATTCAGTCG           60

GGTCCACTAA AAATCTCTAG TGTATCAGAA GTA ATG AAA GAA TCT AAA CAG CCT          114
                                    Met Lys Glu Ser Lys Gln Pro
                                     1               5

GCC TCA CAA CTC CAA AAA CAA AAG GGA GAT ACT CCA GCT TCA GCA ACA           162
Ala Ser Gln Leu Gln Lys Gln Lys Gly Asp Thr Pro Ala Ser Ala Thr
         10                  15                  20

GCA CCT ACA GAA GCG GCT CAA ATT ATT TCT GCA GCA GGT GAT ACC CTG           210
Ala Pro Thr Glu Ala Ala Gln Ile Ile Ser Ala Ala Gly Asp Thr Leu
     25                  30                  35

TCG GTC CCA GCC CCT GCA GTT CAG CCT GAG GAA TCT TTA AAA ACT GAT           258
```

| | | | | | | | | | | | | | | | | |
|---|---|---|---|---|---|---|---|---|---|---|---|---|---|---|---|---|
| Ser | Val | Pro | Ala | Pro | Ala | Val | Gln | Pro | Glu | Glu | Ser | Leu | Lys | Thr | Asp | |
| 40 | | | | 45 | | | | | 50 | | | | | | 55 | |
| CAC | CCT | GAA | ATT | GGT | GAA | GGA | AAA | CCC | ACA | CCT | GCA | CTT | TCA | GAA | GCA | 306 |
| His | Pro | Glu | Ile | Gly | Glu | Gly | Lys | Pro | Thr | Pro | Ala | Leu | Ser | Glu | Ala | |
| | | | | 60 | | | | | 65 | | | | | 70 | | |
| TCC | TCA | TCT | TCT | ATA | AGG | GAG | CGA | CCA | CCT | GAA | GAA | GTT | GCA | GCT | CGC | 354 |
| Ser | Ser | Ser | Ser | Ile | Arg | Glu | Arg | Pro | Pro | Glu | Glu | Val | Ala | Ala | Arg | |
| | | | 75 | | | | | 80 | | | | | 85 | | | |
| CTT | GCA | CAA | CAG | GAA | AAA | CAA | GAA | CAA | GTT | AAA | ATT | GAG | TCT | CTA | GCC | 402 |
| Leu | Ala | Gln | Gln | Glu | Lys | Gln | Glu | Gln | Val | Lys | Ile | Glu | Ser | Leu | Ala | |
| | | 90 | | | | | 95 | | | | | 100 | | | | |
| AAG | AGC | TTA | GAA | GAT | GCT | CTG | AGG | CAA | ACT | GCA | AGT | GTC | ACT | CTG | CAG | 450 |
| Lys | Ser | Leu | Glu | Asp | Ala | Leu | Arg | Gln | Thr | Ala | Ser | Val | Thr | Leu | Gln | |
| | 105 | | | | | 110 | | | | | 115 | | | | | |
| GCT | ATT | GCA | GCT | CAG | AAT | GCT | GCG | GTC | CAG | GCT | GTC | AAT | GCA | CAC | TCC | 498 |
| Ala | Ile | Ala | Ala | Gln | Asn | Ala | Ala | Val | Gln | Ala | Val | Asn | Ala | His | Ser | |
| 120 | | | | | 125 | | | | | 130 | | | | | 135 | |
| AAC | ATA | TTG | AAA | GCC | GCC | ATG | GAC | AAT | TCT | GAG | ATT | GCA | GGC | GAG | AAG | 546 |
| Asn | Ile | Leu | Lys | Ala | Ala | Met | Asp | Asn | Ser | Glu | Ile | Ala | Gly | Glu | Lys | |
| | | | 140 | | | | | 145 | | | | | 150 | | | |
| AAA | TCT | GCT | CAG | TGG | CGC | ACA | GTG | GAG | GGT | GCA | TTG | AAG | GAA | CGC | AGA | 594 |
| Lys | Ser | Ala | Gln | Trp | Arg | Thr | Val | Glu | Gly | Ala | Leu | Lys | Glu | Arg | Arg | |
| | | | 155 | | | | | 160 | | | | | 165 | | | |
| AAG | GCA | GTA | GAT | GAA | GCT | GCC | GAT | GCC | CTT | CTC | AAA | GCC | AAA | GAA | GAG | 642 |
| Lys | Ala | Val | Asp | Glu | Ala | Ala | Asp | Ala | Leu | Leu | Lys | Ala | Lys | Glu | Glu | |
| | | 170 | | | | | 175 | | | | | 180 | | | | |
| TTA | GAG | AAG | ATG | AAA | AGT | GTG | ATT | GAA | AAT | GCA | AAG | AAA | AAA | GAG | GTT | 690 |
| Leu | Glu | Lys | Met | Lys | Ser | Val | Ile | Glu | Asn | Ala | Lys | Lys | Lys | Glu | Val | |
| | 185 | | | | | 190 | | | | | 195 | | | | | |
| GCT | GGG | GCC | AAG | CCT | CAT | ATA | ACT | GCT | GCA | GAG | GGT | AAA | CTT | CAC | AAC | 738 |
| Ala | Gly | Ala | Lys | Pro | His | Ile | Thr | Ala | Ala | Glu | Gly | Lys | Leu | His | Asn | |
| 200 | | | | | 205 | | | | | 210 | | | | | 215 | |
| ATG | ATA | GTT | GAT | CTG | GAT | AAT | GTG | GTC | AAA | AAG | GTC | CAA | GCA | GCT | CAG | 786 |
| Met | Ile | Val | Asp | Leu | Asp | Asn | Val | Val | Lys | Lys | Val | Gln | Ala | Ala | Gln | |
| | | | 220 | | | | | 225 | | | | | 230 | | | |
| TCT | GAG | GCT | AAG | GTT | GTA | TCT | CAG | TAT | CAT | GAG | CTG | GTG | GTC | CAA | GCT | 834 |
| Ser | Glu | Ala | Lys | Val | Val | Ser | Gln | Tyr | His | Glu | Leu | Val | Val | Gln | Ala | |
| | | | 235 | | | | | 240 | | | | | 245 | | | |
| CGG | GAT | GAC | TTT | AAA | CGA | GAG | CTG | GAC | AGT | ATT | ACT | CCA | GAA | GTC | CTT | 882 |
| Arg | Asp | Asp | Phe | Lys | Arg | Glu | Leu | Asp | Ser | Ile | Thr | Pro | Glu | Val | Leu | |
| | | 250 | | | | | 255 | | | | | 260 | | | | |
| CCT | GGG | TGG | AAA | GGA | ATG | AGT | GTT | TCA | GAC | TTA | GCT | GAC | AAG | CTC | TCT | 930 |
| Pro | Gly | Trp | Lys | Gly | Met | Ser | Val | Ser | Asp | Leu | Ala | Asp | Lys | Leu | Ser | |
| | 265 | | | | | 270 | | | | | 275 | | | | | |
| ACT | GAT | GAT | CTG | AAC | TCC | CTC | ATT | GCT | CAT | GCA | CAT | CGT | CGT | ATT | GAT | 978 |
| Thr | Asp | Asp | Leu | Asn | Ser | Leu | Ile | Ala | His | Ala | His | Arg | Arg | Ile | Asp | |
| 280 | | | | | 285 | | | | | 290 | | | | | 295 | |
| CAG | CTG | AAC | AGA | GAG | CTG | GCA | GAA | CAG | AAG | GCC | ACC | GAA | AAG | CAG | CAC | 1026 |
| Gln | Leu | Asn | Arg | Glu | Leu | Ala | Glu | Gln | Lys | Ala | Thr | Glu | Lys | Gln | His | |
| | | | | 300 | | | | | 305 | | | | | 310 | | |
| ATC | ACG | TTA | GCC | TTG | GAG | AAA | CAA | AAG | CTG | GAA | GAA | AAG | CGG | GCA | TTT | 1074 |
| Ile | Thr | Leu | Ala | Leu | Glu | Lys | Gln | Lys | Leu | Glu | Glu | Lys | Arg | Ala | Phe | |
| | | | 315 | | | | | 320 | | | | | 325 | | | |
| GAC | TCT | GCA | GTA | GCA | AAA | GCA | TTA | GAA | CAT | CAC | AGA | AGT | GAA | ATA | CAG | 1122 |
| Asp | Ser | Ala | Val | Ala | Lys | Ala | Leu | Glu | His | His | Arg | Ser | Glu | Ile | Gln | |
| | | 330 | | | | | 335 | | | | | 340 | | | | |
| GCT | GAA | CAG | GAC | AGA | AAG | ATA | GAA | GAA | GTC | AGA | GAT | GCC | ATG | GAA | AAT | 1170 |
| Ala | Glu | Gln | Asp | Arg | Lys | Ile | Glu | Glu | Val | Arg | Asp | Ala | Met | Glu | Asn | |
| | 345 | | | | | 350 | | | | | 355 | | | | | |
| GAA | ATG | AGA | ACC | CCT | TCG | CCG | ACA | GCA | GCT | GCC | CAC | ACT | GAT | CAC | TTG | 1218 |

```
Glu Met Arg Thr Pro Ser Pro Thr Ala Ala Ala His Thr Asp His Leu
360             365             370             375

CGA GAT GTC CTT AGG GTA CAA GAA CAG GAA TTG AAG TCT GAA TTT GAG    1266
Arg Asp Val Leu Arg Val Gln Glu Gln Glu Leu Lys Ser Glu Phe Glu
            380             385             390

CAG AAC CTG TCT GAG AAA CTC TCT GAA CAA GAA TTA CAA TTT CGT CGT    1314
Gln Asn Leu Ser Glu Lys Leu Ser Glu Gln Glu Leu Gln Phe Arg Arg
                395             400             405

CTC AGT CAA GAG CAA GTT GAC AAC TTT ACT CTG GAT ATA AAT ACT GCC    1362
Leu Ser Gln Glu Gln Val Asp Asn Phe Thr Leu Asp Ile Asn Thr Ala
            410             415             420

TAT GCC AGA CTC AGA GGA ATC GAA CAG GCT GTT CAG AGC CAT GCA GTT    1410
Tyr Ala Arg Leu Arg Gly Ile Glu Gln Ala Val Gln Ser His Ala Val
        425             430             435

GCT GAA GAG GAA GCC AGA AAA GCC CAC CAA CTC TGG CTT TCA GTG GAG    1458
Ala Glu Glu Glu Ala Arg Lys Ala His Gln Leu Trp Leu Ser Val Glu
440             445             450             455

GCA TTA AAG TAC AGC ATG AAG ACC TCA TCT GCA GAA ACA CCT ACT ATC    1506
Ala Leu Lys Tyr Ser Met Lys Thr Ser Ser Ala Glu Thr Pro Thr Ile
            460             465             470

CCG CTG GGT AGT GCG GTT GAG GCC ATC AAA GCC AAC TGT TCT GAT AAT    1554
Pro Leu Gly Ser Ala Val Glu Ala Ile Lys Ala Asn Cys Ser Asp Asn
        475             480             485

GAA TTC ACC CAA GCT TTA ACC GCA GCT ATC CCT CCA GAG TCC CTG ACC    1602
Glu Phe Thr Gln Ala Leu Thr Ala Ala Ile Pro Pro Glu Ser Leu Thr
        490             495             500

CGT GGG GTG TAC AGT GAA GAG ACC CTT AGA GCC CGT TTC TAT GCT GTT    1650
Arg Gly Val Tyr Ser Glu Glu Thr Leu Arg Ala Arg Phe Tyr Ala Val
505             510             515

CAA AAA CTG GCC CGA AGG GTA GCA ATG ATT GAT GAA ACC AGA AAT AGC    1698
Gln Lys Leu Ala Arg Arg Val Ala Met Ile Asp Glu Thr Arg Asn Ser
520             525             530             535

TTG TAC CAG TAC TTC CTC TCC TAC CTA CAG TCC CTG CTC CTA TTC CCA    1746
Leu Tyr Gln Tyr Phe Leu Ser Tyr Leu Gln Ser Leu Leu Leu Phe Pro
            540             545             550

CCT CAG CAA CTG AAG CCG CCC CCA GAG CTC TGC CCT GAG GAT ATA AAC    1794
Pro Gln Gln Leu Lys Pro Pro Pro Glu Leu Cys Pro Glu Asp Ile Asn
        555             560             565

ACA TTT AAA TTA CTG TCA TAT GCT TCC TAT TGC ATT GAG CAT GGT GAT    1842
Thr Phe Lys Leu Leu Ser Tyr Ala Ser Tyr Cys Ile Glu His Gly Asp
        570             575             580

CTG GAG CTA GCA GCA AAG TTT GTC AAT CAG CTG AAG GGG GAA TCC AGA    1890
Leu Glu Leu Ala Ala Lys Phe Val Asn Gln Leu Lys Gly Glu Ser Arg
585             590             595

CGA GTG GCA CAG GAC TGG CTG AAG GAA GCC CGA ATG ACC CTA GAA ACG    1938
Arg Val Ala Gln Asp Trp Leu Lys Glu Ala Arg Met Thr Leu Glu Thr
600             605             610             615

AAA CAG ATA GTG GAA ATC CTG ACA GCA TAT GCC AGC GCC GTA GGA ATA    1986
Lys Gln Ile Val Glu Ile Leu Thr Ala Tyr Ala Ser Ala Val Gly Ile
            620             625             630

GGA ACC ACT CAG GTG CAG CCA GAG TGAGGTTTAG GAAGATTTTC ATAAAGTCAT   2040
Gly Thr Thr Gln Val Gln Pro Glu
                635

ATTTCATGTC AAAGGAAATC AGCAGTGATA GATGAAGGGT TCGCAGCGAG AGTCCCGGAC  2100

TTGTCTAGAA ATGAGCAGGT TTACAAGTAC TGTTCTAAAT GTTAACACCT GTTGCATTTA  2160

TATTCTTTCC ATTTGCTATC ATGTCAGTGA ACGCCAGGAG TGCTTTCTTT GCAACTTGTG  2220

TAACATTTTC TGTTTTTTCA GGTTTTACTG ATGAGGCTTG TGAGGCCAAT CAAAATAATG  2280

TTTGTGATCT CTACTACTGT TGATTTTGCC CTCGGAGCAA ACTGAATAAA GCAACAAGAT  2340
```

```
GAAAAAAAAA AAAAAAAAA                                                                      2360
```

( 2 ) INFORMATION FOR SEQ ID NO:2:

( i ) SEQUENCE CHARACTERISTICS:
        ( A ) LENGTH: 639 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Lys Glu Ser Lys Gln Pro Ala Ser Gln Leu Gln Lys Gln Lys Gly
 1               5                  10                  15

Asp Thr Pro Ala Ser Ala Thr Ala Pro Thr Glu Ala Ala Gln Ile Ile
             20                  25                  30

Ser Ala Ala Gly Asp Thr Leu Ser Val Pro Ala Pro Ala Val Gln Pro
         35                  40                  45

Glu Glu Ser Leu Lys Thr Asp His Pro Glu Ile Gly Glu Gly Lys Pro
     50                  55                  60

Thr Pro Ala Leu Ser Glu Ala Ser Ser Ser Ile Arg Glu Arg Pro
 65                  70                  75                  80

Pro Glu Glu Val Ala Ala Arg Leu Ala Gln Gln Glu Lys Gln Glu Gln
                 85                  90                  95

Val Lys Ile Glu Ser Leu Ala Lys Ser Leu Glu Asp Ala Leu Arg Gln
            100                 105                 110

Thr Ala Ser Val Thr Leu Gln Ala Ile Ala Ala Gln Asn Ala Ala Val
            115                 120                 125

Gln Ala Val Asn Ala His Ser Asn Ile Leu Lys Ala Ala Met Asp Asn
        130                 135                 140

Ser Glu Ile Ala Gly Glu Lys Lys Ser Ala Gln Trp Arg Thr Val Glu
145                 150                 155                 160

Gly Ala Leu Lys Glu Arg Arg Lys Ala Val Asp Glu Ala Ala Asp Ala
                165                 170                 175

Leu Leu Lys Ala Lys Glu Glu Leu Glu Lys Met Lys Ser Val Ile Glu
            180                 185                 190

Asn Ala Lys Lys Lys Glu Val Ala Gly Ala Lys Pro His Ile Thr Ala
        195                 200                 205

Ala Glu Gly Lys Leu His Asn Met Ile Val Asp Leu Asp Asn Val Val
    210                 215                 220

Lys Lys Val Gln Ala Ala Gln Ser Glu Ala Lys Val Val Ser Gln Tyr
225                 230                 235                 240

His Glu Leu Val Val Gln Ala Arg Asp Asp Phe Lys Arg Glu Leu Asp
                245                 250                 255

Ser Ile Thr Pro Glu Val Leu Pro Gly Trp Lys Gly Met Ser Val Ser
            260                 265                 270

Asp Leu Ala Asp Lys Leu Ser Thr Asp Asp Leu Asn Ser Leu Ile Ala
        275                 280                 285

His Ala His Arg Arg Ile Asp Gln Leu Asn Arg Glu Leu Ala Glu Gln
    290                 295                 300

Lys Ala Thr Glu Lys Gln His Ile Thr Leu Ala Leu Glu Lys Gln Lys
305                 310                 315                 320

Leu Glu Glu Lys Arg Ala Phe Asp Ser Ala Val Ala Lys Ala Leu Glu
                325                 330                 335

His His Arg Ser Glu Ile Gln Ala Glu Gln Asp Arg Lys Ile Glu Glu
            340                 345                 350
```

| | | | | | | | | | | | | | | |
|---|---|---|---|---|---|---|---|---|---|---|---|---|---|---|
|Val|Arg|Asp<br>355|Ala|Met|Glu|Asn<br>360|Glu|Met|Arg|Thr|Pro<br>365|Ser|Pro|Thr|Ala|
|Ala|Ala<br>370|His|Thr|Asp|His<br>375|Leu|Arg|Asp|Val|Leu<br>380|Arg|Val|Gln|Glu|Gln|
|Glu<br>385|Leu|Lys|Ser|Glu|Phe<br>390|Glu|Gln|Asn|Leu|Ser<br>395|Glu|Lys|Leu|Ser|Glu<br>400|
|Gln|Glu|Leu|Gln|Phe<br>405|Arg|Arg|Leu|Ser|Gln<br>410|Glu|Gln|Val|Asp|Asn<br>415|Phe|
|Thr|Leu|Asp|Ile<br>420|Asn|Thr|Ala|Tyr|Ala<br>425|Arg|Leu|Arg|Gly|Ile<br>430|Glu|Gln|
|Ala|Val|Gln<br>435|Ser|His|Ala|Val<br>440|Ala|Glu|Glu|Glu|Ala<br>445|Arg|Lys|Ala|His|
|Gln|Leu<br>450|Trp|Leu|Ser|Val|Glu<br>455|Ala|Leu|Lys|Tyr|Ser<br>460|Met|Lys|Thr|Ser|
|Ser<br>465|Ala|Glu|Thr|Pro|Thr<br>470|Ile|Pro|Leu|Gly|Ser<br>475|Ala|Val|Glu|Ala|Ile<br>480|
|Lys|Ala|Asn|Cys|Ser<br>485|Asp|Asn|Glu|Phe|Thr<br>490|Gln|Ala|Leu|Thr|Ala<br>495|Ala|
|Ile|Pro|Pro|Glu<br>500|Ser|Leu|Thr|Arg|Gly<br>505|Val|Tyr|Ser|Glu|Glu<br>510|Thr|Leu|
|Arg|Ala|Arg<br>515|Phe|Tyr|Ala|Val<br>520|Gln|Lys|Leu|Ala|Arg<br>525|Arg|Val|Ala|Met|
|Ile|Asp<br>530|Glu|Thr|Arg|Asn<br>535|Ser|Leu|Tyr|Gln|Tyr<br>540|Phe|Leu|Ser|Tyr|Leu|
|Gln<br>545|Ser|Leu|Leu|Leu|Phe<br>550|Pro|Pro|Gln|Gln|Leu<br>555|Lys|Pro|Pro|Pro|Glu<br>560|
|Leu|Cys|Pro|Glu|Asp<br>565|Ile|Asn|Thr|Phe|Lys<br>570|Leu|Leu|Ser|Tyr|Ala<br>575|Ser|
|Tyr|Cys|Ile|Glu|His<br>580|Gly|Asp|Leu|Glu|Leu<br>585|Ala|Ala|Lys|Phe|Val<br>590|Asn|
|Gln|Leu|Lys|Gly<br>595|Glu|Ser|Arg|Arg<br>600|Val|Ala|Gln|Asp|Trp<br>605|Leu|Lys|Glu|
|Ala|Arg<br>610|Met|Thr|Leu|Glu|Thr<br>615|Lys|Gln|Ile|Val|Glu<br>620|Ile|Leu|Thr|Ala|
|Tyr<br>625|Ala|Ser|Ala|Val|Gly<br>630|Ile|Gly|Thr|Thr|Gln<br>635|Val|Gln|Pro|Glu|

( 2 ) INFORMATION FOR SEQ ID NO:3:

( i ) SEQUENCE CHARACTERISTICS:
        ( A ) LENGTH: 6306 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..6306

( x ) PUBLICATION INFORMATION:
        ( A ) AUTHORS: COMPTON, DUANE A
                  SZILAK, ILYA
                  CLEVELAND, DON W
        ( B ) TITLE: PRIMARY STRUCTURE OF NUMA, AN INTRANUCLEAR
             PROTEIN THAT DEFINES A NOVEL PATHWAY FOR
             SEGREGATION OF PROTEINS AT MITOSIS
        ( C ) JOURNAL: J. Cell Biol.
        ( D ) VOLUME: 116
        ( F ) PAGES: 1395-1408

( G ) DATE: 1992

( x i ) SEQUENCE DESCRIPTION: SEQ ID NO:3:

```
ATG ACA CTC CAC GCC ACC CGG GGG GCT GCA CTC CTC TCT TGG GTG AAC        48
Met Thr Leu His Ala Thr Arg Gly Ala Ala Leu Leu Ser Trp Val Asn
 1               5                  10                  15

AGT CTA CAC GTG GCT GAC CCT GTG GAG GCT GTG CTG CAG CTC CAG GAC        96
Ser Leu His Val Ala Asp Pro Val Glu Ala Val Leu Gln Leu Gln Asp
             20                  25                  30

TGC AGC ATC TTC ATC AAG ATC ATT GAC AGA ATC CAT GGC ACT GAA GAG       144
Cys Ser Ile Phe Ile Lys Ile Ile Asp Arg Ile His Gly Thr Glu Glu
                 35                  40                  45

GGA CAG CAA ATC TTG AAG CAG CCG GTG TCA GAG AGA CTG GAC TTT GTG       192
Gly Gln Gln Ile Leu Lys Gln Pro Val Ser Glu Arg Leu Asp Phe Val
         50                  55                  60

TGC AGT TTT CTG CAG AAA AAT CGA AAA CAT CCC TCT TCC CCA GAA TGC       240
Cys Ser Phe Leu Gln Lys Asn Arg Lys His Pro Ser Ser Pro Glu Cys
 65                  70                  75                  80

CTG GTA TCT GCA CAG AAG GTG CTA GAG GGA TCA GAG CTG GAA CTG GCG       288
Leu Val Ser Ala Gln Lys Val Leu Glu Gly Ser Glu Leu Glu Leu Ala
                 85                  90                  95

AAG ATG ACC ATG CTG CTC TTA TAC CAC TCT ACC ATG AGC TCC AAA AGT       336
Lys Met Thr Met Leu Leu Leu Tyr His Ser Thr Met Ser Ser Lys Ser
            100                 105                 110

CCC AGG GAC TGG GAA CAG TTT GAA TAT AAA ATT CAG GCT GAG TTG GCT       384
Pro Arg Asp Trp Glu Gln Phe Glu Tyr Lys Ile Gln Ala Glu Leu Ala
        115                 120                 125

GTC ATT CTT AAA TTT GTG CTG GAC CAT GAG GAC GGG CTA AAC CTT AAT       432
Val Ile Leu Lys Phe Val Leu Asp His Glu Asp Gly Leu Asn Leu Asn
130                 135                 140

GAG GAC CTA GAG AAC TTC CTA CAG AAA GCT CCT GTG CCT TCT ACC TGT       480
Glu Asp Leu Glu Asn Phe Leu Gln Lys Ala Pro Val Pro Ser Thr Cys
145                 150                 155                 160

TCT AGC ACA TTC CCT GAA GAG CTC TCC CCA CCT AGC CAC CAG GCC AAG       528
Ser Ser Thr Phe Pro Glu Glu Leu Ser Pro Pro Ser His Gln Ala Lys
                165                 170                 175

AGG GAG ATT CGC TTC CTA GAG CTA CAG AAG GTT GCC TCC TCT TCC AGT       576
Arg Glu Ile Arg Phe Leu Glu Leu Gln Lys Val Ala Ser Ser Ser Ser
            180                 185                 190

GGG AAC AAC TTT CTC TCA GGT TCT CCA GCT TCT CCC ATG GGT GAT ATC       624
Gly Asn Asn Phe Leu Ser Gly Ser Pro Ala Ser Pro Met Gly Asp Ile
        195                 200                 205

CTG CAG ACC CCA CAG TTC CAG ATG AGA CGG CTG AAG AAG CAG CTT GCT       672
Leu Gln Thr Pro Gln Phe Gln Met Arg Arg Leu Lys Lys Gln Leu Ala
    210                 215                 220

GAT GAG AGA AGT AAT AGG GAT GAG CTG GAG CTG GAG CTA GCT GAG AAC       720
Asp Glu Arg Ser Asn Arg Asp Glu Leu Glu Leu Glu Leu Ala Glu Asn
225                 230                 235                 240

CGC AAG CTC CTC ACC GAG AAG GAT GCA CAG ATA GCC ATG ATG CAG CAG       768
Arg Lys Leu Leu Thr Glu Lys Asp Ala Gln Ile Ala Met Met Gln Gln
                245                 250                 255

CGC ATT GAC CGC CTA GCC CTG CTG AAT GAG AAG CAG GCG GCC AGC CCA       816
Arg Ile Asp Arg Leu Ala Leu Leu Asn Glu Lys Gln Ala Ala Ser Pro
            260                 265                 270

CTG GAG CCC AAG GAG CTT GAG GAG CTG CGT GAC AAG AAT GAG AGC CTT       864
Leu Glu Pro Lys Glu Leu Glu Glu Leu Arg Asp Lys Asn Glu Ser Leu
        275                 280                 285

ACC ATG CGG CTG CAT GAA ACC CTG AAG CAG TGC CAG GAC CTG AAG ACA       912
Thr Met Arg Leu His Glu Thr Leu Lys Gln Cys Gln Asp Leu Lys Thr
    290                 295                 300
```

| | | | | | | | | | | | | | | | | |
|---|---|---|---|---|---|---|---|---|---|---|---|---|---|---|---|---|
| GAG | AAG | AGC | CAG | ATG | GAT | CGC | AAA | ATC | AAC | CAG | CTT | TCG | GAG | GAG | AAT | 960 |
| Glu | Lys | Ser | Gln | Met | Asp | Arg | Lys | Ile | Asn | Gln | Leu | Ser | Glu | Glu | Asn | |
| 305 | | | | 310 | | | | | 315 | | | | | 320 | | |
| GGA | GAC | CTT | TCC | TTT | AAG | CTG | CGG | GAG | TTT | GCC | AGT | CAT | CTG | CAG | CAG | 1008 |
| Gly | Asp | Leu | Ser | Phe | Lys | Leu | Arg | Glu | Phe | Ala | Ser | His | Leu | Gln | Gln | |
| | | | | 325 | | | | | 330 | | | | | 335 | | |
| CTA | CAG | GAT | GCC | CTC | AAT | GAG | CTG | ACG | GAG | GAG | CAC | AGC | AAG | GCC | ACT | 1056 |
| Leu | Gln | Asp | Ala | Leu | Asn | Glu | Leu | Thr | Glu | Glu | His | Ser | Lys | Ala | Thr | |
| | | | 340 | | | | | 345 | | | | | 350 | | | |
| CAG | GAG | TGG | CTA | GAG | AAG | CAG | GCC | CAG | CTG | GAG | AAG | GAG | CTC | AGC | GCA | 1104 |
| Gln | Glu | Trp | Leu | Glu | Lys | Gln | Ala | Gln | Leu | Glu | Lys | Glu | Leu | Ser | Ala | |
| | | 355 | | | | | 360 | | | | | 365 | | | | |
| GCC | CTG | CAG | GAC | AAG | AAA | TGC | CTT | GAA | GAG | AAG | AAC | GAA | ATC | CTT | CAG | 1152 |
| Ala | Leu | Gln | Asp | Lys | Lys | Cys | Leu | Glu | Glu | Lys | Asn | Glu | Ile | Leu | Gln | |
| 370 | | | | | 375 | | | | | 380 | | | | | | |
| GGA | AAA | CTT | TCA | CAG | CTG | GAA | GAA | CAC | TTG | TCC | CAG | CTG | CAG | GAT | AAC | 1200 |
| Gly | Lys | Leu | Ser | Gln | Leu | Glu | Glu | His | Leu | Ser | Gln | Leu | Gln | Asp | Asn | |
| 385 | | | | | 390 | | | | | 395 | | | | | 400 | |
| CCA | CCC | CAG | GAG | AAG | GGC | GAG | GTG | CTG | GGT | GAT | GTC | TTG | CAG | CTG | GAA | 1248 |
| Pro | Pro | Gln | Glu | Lys | Gly | Glu | Val | Leu | Gly | Asp | Val | Leu | Gln | Leu | Glu | |
| | | | | 405 | | | | | 410 | | | | | 415 | | |
| ACC | TTG | AAG | CAA | GAG | GCA | GCC | ACT | CTT | GCT | GCA | AAC | AAC | ACA | CAG | CTC | 1296 |
| Thr | Leu | Lys | Gln | Glu | Ala | Ala | Thr | Leu | Ala | Ala | Asn | Asn | Thr | Gln | Leu | |
| | | | 420 | | | | | 425 | | | | | 430 | | | |
| CAA | GCC | AGG | GTA | GAG | ATG | CTG | GAG | ACT | GAG | CGA | GGC | CAG | CAG | GAA | GCC | 1344 |
| Gln | Ala | Arg | Val | Glu | Met | Leu | Glu | Thr | Glu | Arg | Gly | Gln | Gln | Glu | Ala | |
| | | 435 | | | | | 440 | | | | | 445 | | | | |
| AAG | CTG | CTT | GCT | GAG | CGG | GGC | CAC | TTC | GAA | GAA | GAA | AAG | CAG | CAG | CTG | 1392 |
| Lys | Leu | Leu | Ala | Glu | Arg | Gly | His | Phe | Glu | Glu | Glu | Lys | Gln | Gln | Leu | |
| | 450 | | | | | 455 | | | | | 460 | | | | | |
| TCT | AGC | CTG | ATC | ACT | GAC | CTG | CAG | AGC | TCC | ATC | TCC | AAC | CTC | AGC | CAG | 1440 |
| Ser | Ser | Leu | Ile | Thr | Asp | Leu | Gln | Ser | Ser | Ile | Ser | Asn | Leu | Ser | Gln | |
| 465 | | | | | 470 | | | | | 475 | | | | | 480 | |
| GCC | AAG | GAA | GAG | CTG | GAG | CAG | GCC | TCC | CAG | GCT | CAT | GGG | GCC | CGG | TTG | 1488 |
| Ala | Lys | Glu | Glu | Leu | Glu | Gln | Ala | Ser | Gln | Ala | His | Gly | Ala | Arg | Leu | |
| | | | | 485 | | | | | 490 | | | | | 495 | | |
| ACT | GCC | CAG | GTG | GCC | TCT | CTG | ACC | TCT | GAG | CTC | ACC | ACA | CTC | AAT | GCC | 1536 |
| Thr | Ala | Gln | Val | Ala | Ser | Leu | Thr | Ser | Glu | Leu | Thr | Thr | Leu | Asn | Ala | |
| | | | 500 | | | | | 505 | | | | | 510 | | | |
| ACC | ATC | CAG | CAA | CAG | GAT | CAA | GAA | CTG | GCT | GGC | CTG | AAG | CAG | CAG | GCC | 1584 |
| Thr | Ile | Gln | Gln | Gln | Asp | Gln | Glu | Leu | Ala | Gly | Leu | Lys | Gln | Gln | Ala | |
| | | | 515 | | | | | 520 | | | | | 525 | | | |
| AAA | GAG | AAG | CAG | GCC | CAG | CTA | GCA | CAG | ACC | CTC | CAA | CAG | CAA | GAA | CAG | 1632 |
| Lys | Glu | Lys | Gln | Ala | Gln | Leu | Ala | Gln | Thr | Leu | Gln | Gln | Gln | Glu | Gln | |
| | 530 | | | | | 535 | | | | | 540 | | | | | |
| GCC | TCC | CAG | GGC | CTC | CGC | CAC | CAG | GTG | GAG | CAG | CTA | AGC | AGT | AGC | CTG | 1680 |
| Ala | Ser | Gln | Gly | Leu | Arg | His | Gln | Val | Glu | Gln | Leu | Ser | Ser | Ser | Leu | |
| 545 | | | | | 550 | | | | | 555 | | | | | 560 | |
| AAG | CAG | AAG | GAG | CAG | CAG | TTG | AAG | GAG | GTA | GCG | GAG | AAG | CAG | GAG | GCA | 1728 |
| Lys | Gln | Lys | Glu | Gln | Gln | Leu | Lys | Glu | Val | Ala | Glu | Lys | Gln | Glu | Ala | |
| | | | | 565 | | | | | 570 | | | | | 575 | | |
| ACT | AGG | CAG | GAC | CAT | GCC | CAG | CAA | CTG | GCC | ACT | GCT | GCA | GAG | GAG | CGA | 1776 |
| Thr | Arg | Gln | Asp | His | Ala | Gln | Gln | Leu | Ala | Thr | Ala | Ala | Glu | Glu | Arg | |
| | | | 580 | | | | | 585 | | | | | 590 | | | |
| GAG | GCC | TCC | TTA | AGG | GAG | CGG | GAT | GCG | GCT | CTC | AAG | CAG | CTG | GAG | GCA | 1824 |
| Glu | Ala | Ser | Leu | Arg | Glu | Arg | Asp | Ala | Ala | Leu | Lys | Gln | Leu | Glu | Ala | |
| | | 595 | | | | | 600 | | | | | 605 | | | | |
| CTG | GAG | AAG | GAG | AAG | GCT | GCC | AAG | CTG | GAG | ATT | CTG | CAG | CAG | CAA | CTT | 1872 |
| Leu | Glu | Lys | Glu | Lys | Ala | Ala | Lys | Leu | Glu | Ile | Leu | Gln | Gln | Gln | Leu | |
| 610 | | | | | 615 | | | | | 620 | | | | | | |

```
CAG GTG GCT AAT GAA GCC CGG GAC AGT GCC CAG ACC TCA GTG ACA CAG        1920
Gln Val Ala Asn Glu Ala Arg Asp Ser Ala Gln Thr Ser Val Thr Gln
625             630                 635                 640

GCC CAG CGG GAG AAG GCA GAG CTG AGC CGG AAG GTG GAG GAA CTC CAG        1968
Ala Gln Arg Glu Lys Ala Glu Leu Ser Arg Lys Val Glu Glu Leu Gln
                645                 650                 655

GCC TGT GTT GAG ACA GCC CGC CAG GAA CAG CAT GAG GCC CAG GCC CAG        2016
Ala Cys Val Glu Thr Ala Arg Gln Glu Gln His Glu Ala Gln Ala Gln
                660                 665                 670

GTT GCA GAG CTA GAG TTG CAG CTG CGG TCT GAG CAG CAA AAA GCA ACT        2064
Val Ala Glu Leu Glu Leu Gln Leu Arg Ser Glu Gln Gln Lys Ala Thr
            675                 680                 685

GAG AAA GAA AGG GTG GCC CAG GAG AAG GAC CAG CTC CAG GAG CAG CTC        2112
Glu Lys Glu Arg Val Ala Gln Glu Lys Asp Gln Leu Gln Glu Gln Leu
690                 695                 700

CAG GCC CTC AAA GAG TCC TTG AAG GTC ACC AAG GGC AGC CTT GAA GAG        2160
Gln Ala Leu Lys Glu Ser Leu Lys Val Thr Lys Gly Ser Leu Glu Glu
705                 710                 715                 720

GAG AAG CGC AGG GCT GCA GAT GCC CTG GAA GAG CAG CAG CGT TGT ATC        2208
Glu Lys Arg Arg Ala Ala Asp Ala Leu Glu Glu Gln Gln Arg Cys Ile
                725                 730                 735

TCT GAG CTG AAG GCA GAG ACC CGA AGC CTG GTG GAG CAG CAT AAG CGG        2256
Ser Glu Leu Lys Ala Glu Thr Arg Ser Leu Val Glu Gln His Lys Arg
                740                 745                 750

GAA CGA AAG GAG CTG GAA GAA GAG AGG GCT GGG CGC AAG GGG CTG GAG        2304
Glu Arg Lys Glu Leu Glu Glu Glu Arg Ala Gly Arg Lys Gly Leu Glu
            755                 760                 765

GCT CGA TTA CTG CAG CTT GGG GAG GCC CAT CAG GCT GAG ACT GAA GTC        2352
Ala Arg Leu Leu Gln Leu Gly Glu Ala His Gln Ala Glu Thr Glu Val
770                 775                 780

CTG CGG CGG GAG CTG GCA GAG GCC ATG GCT GCC CAG CAC ACA GCT GAG        2400
Leu Arg Arg Glu Leu Ala Glu Ala Met Ala Ala Gln His Thr Ala Glu
785                 790                 795                 800

AGT GAG TGT GAG CAG CTC GTC AAA GAA GTA GCT GCC TGG CGT GAC GGG        2448
Ser Glu Cys Glu Gln Leu Val Lys Glu Val Ala Ala Trp Arg Asp Gly
                805                 810                 815

TAT GAG GAT AGC CAG CAA GAG GAG GCA CAG TAT GGC GCC ATG TTC CAG        2496
Tyr Glu Asp Ser Gln Gln Glu Glu Ala Gln Tyr Gly Ala Met Phe Gln
                820                 825                 830

GAA CAG CTG ATG ACT TTG AAG GAG GAA TGT GAG AAG GCC CGC CAG GAG        2544
Glu Gln Leu Met Thr Leu Lys Glu Glu Cys Glu Lys Ala Arg Gln Glu
            835                 840                 845

CTG CAG GAG GCA AAG GAG AAG GTG GCA GGC ATA GAA TCC CAC AGC GAG        2592
Leu Gln Glu Ala Lys Glu Lys Val Ala Gly Ile Glu Ser His Ser Glu
850                 855                 860

CTC CAG ATA AGC CGG CAG CAG AAC AAA CTA GCT GAG CTC CAT GCC AAC        2640
Leu Gln Ile Ser Arg Gln Gln Asn Lys Leu Ala Glu Leu His Ala Asn
865                 870                 875                 880

CTG GCC AGA GCA CTC CAG CAG GTC CAA GAG AAG GAA GTC AGG GCC CAG        2688
Leu Ala Arg Ala Leu Gln Gln Val Gln Glu Lys Glu Val Arg Ala Gln
                885                 890                 895

AAG CTT GCA GAT GAC CTC TCC ACT CTG CAG GAA AAG ATG GCT GCC ACC        2736
Lys Leu Ala Asp Asp Leu Ser Thr Leu Gln Glu Lys Met Ala Ala Thr
                900                 905                 910

AGC AAA GAG GTG GCC CGC TTG GAG ACC TTG GTC CGC AAG GCA GGT GAG        2784
Ser Lys Glu Val Ala Arg Leu Glu Thr Leu Val Arg Lys Ala Gly Glu
            915                 920                 925

CAG CAG GAA ACA GCC TCC CGG GAG TTA GTC AAG GAG CCT GCG AGG GCA        2832
Gln Gln Glu Thr Ala Ser Arg Glu Leu Val Lys Glu Pro Ala Arg Ala
930                 935                 940
```

```
GGA GAC AGA CAG CCC GAG TGG CTG GAA GAG CAA CAG GGA CGC CAG TTC                    2880
Gly Asp Arg Gln Pro Glu Trp Leu Glu Glu Gln Gln Gly Arg Gln Phe
945                 950                 955                 960

TGC AGC ACA CAG GCA GCG CTG CAG GCT ATG GAG CGG GAG GCA GAG CAG                    2928
Cys Ser Thr Gln Ala Ala Leu Gln Ala Met Glu Arg Glu Ala Glu Gln
            965                 970                 975

ATG GGC AAT GAG CTG GAA CGG CTG CGG GCC GCG CTG ATG GAG AGC CAG                    2976
Met Gly Asn Glu Leu Glu Arg Leu Arg Ala Ala Leu Met Glu Ser Gln
                980                 985                 990

GGG CAG CAG CAG GAG GAG CGT GGG CAG CAG GAA AGG GAG GTG GCG CGG                    3024
Gly Gln Gln Gln Glu Glu Arg Gly Gln Gln Glu Arg Glu Val Ala Arg
            995                 1000                1005

CTG ACC CAG GAG CGG GGC CGT GCC CAG GCT GAC CTT GCC CTG GAG AAG                    3072
Leu Thr Gln Glu Arg Gly Arg Ala Gln Ala Asp Leu Ala Leu Glu Lys
                1010                1015                1020

GCG GCC AGA GCA GAG CTT GAG ATG CGG CTG CAG AAC GCC CTC AAC GAG                    3120
Ala Ala Arg Ala Glu Leu Glu Met Arg Leu Gln Asn Ala Leu Asn Glu
1025                1030                1035                1040

CAG CGT GTG GAG TTC GCT ACC CTG CAA GAG GCA CTG GCT CAT GCC CTG                    3168
Gln Arg Val Glu Phe Ala Thr Leu Gln Glu Ala Leu Ala His Ala Leu
                1045                1050                1055

ACG GAA AAG GAA GGC AAG GAC CAG GAG TTG GCC AAG CTT CGT GGT CTG                    3216
Thr Glu Lys Glu Gly Lys Asp Gln Glu Leu Ala Lys Leu Arg Gly Leu
                1060                1065                1070

GAG GCA GCC CAG ATA AAA GAG CTG GAG GAA CTT CGG CAA ACC GTG AAG                    3264
Glu Ala Ala Gln Ile Lys Glu Leu Glu Glu Leu Arg Gln Thr Val Lys
1075                1080                1085

CAA CTG AAG GAA CAG CTG GCT AAG AAA GAA AAG GAG CAC GCA TCT GGC                    3312
Gln Leu Lys Glu Gln Leu Ala Lys Lys Glu Lys Glu His Ala Ser Gly
    1090                1095                1100

TCA GGA GCC CAA TCT GAG GCT GCT GGC AGG ACA GAG CCA ACA GGC CCC                    3360
Ser Gly Ala Gln Ser Glu Ala Ala Gly Arg Thr Glu Pro Thr Gly Pro
1105                1110                1115                1120

AAG CTG GAA GCA CTG CGG GCA GAG GTG AGC AAG CTG GAA CAG CAA TGC                    3408
Lys Leu Glu Ala Leu Arg Ala Glu Val Ser Lys Leu Glu Gln Gln Cys
                1125                1130                1135

CAG AAG CAG CAG GAG CAG GCT GAC AGC CTG GAA CGC AGC CTC GAG GCT                    3456
Gln Lys Gln Gln Glu Gln Ala Asp Ser Leu Glu Arg Ser Leu Glu Ala
        1140                1145                1150

GAG CGG GCC TCC CGG GCT GAG CGG GAC AGT GCT CTG GAG ACT CTG CAG                    3504
Glu Arg Ala Ser Arg Ala Glu Arg Asp Ser Ala Leu Glu Thr Leu Gln
        1155                1160                1165

GGC CAG TTA GAG GAG AAG GCC CAG GAG CTA GGG CAC AGT CAG AGT GCC                    3552
Gly Gln Leu Glu Glu Lys Ala Gln Glu Leu Gly His Ser Gln Ser Ala
    1170                1175                1180

TTA GCC TCG GCC CAA CGG GAG TTG GCT GCC TTC CGC ACC AAG GTA CAA                    3600
Leu Ala Ser Ala Gln Arg Glu Leu Ala Ala Phe Arg Thr Lys Val Gln
1185                1190                1195                1200

GAC CAC AGC AAG GCT GAA GAT GAG TGG AAG GCC CAG GTG GCC CGG GGC                    3648
Asp His Ser Lys Ala Glu Asp Glu Trp Lys Ala Gln Val Ala Arg Gly
                1205                1210                1215

CGG CAA GAG GCT GAG AGG AAA AAT AGC CTC ATC AGC AGC TTG GAG GAG                    3696
Arg Gln Glu Ala Glu Arg Lys Asn Ser Leu Ile Ser Ser Leu Glu Glu
        1220                1225                1230

GAG GTG TCC ATC CTG AAT CGC CAG GTC CTG GAG AAG GAG GGG GAG AGC                    3744
Glu Val Ser Ile Leu Asn Arg Gln Val Leu Glu Lys Glu Gly Glu Ser
            1235                1240                1245

AAG GAG TTG AAG CGG CTG GTG ATG GCC GAG TCA GAG AAG AGC CAG AAG                    3792
Lys Glu Leu Lys Arg Leu Val Met Ala Glu Ser Glu Lys Ser Gln Lys
                1250                1255                1260
```

-continued

| | | | | | | | | | | | | | | | | |
|---|---|---|---|---|---|---|---|---|---|---|---|---|---|---|---|---|
| CTG | GAG | GAG | AGC | TGC | GCC | TGC | TGC | AGG | CAG | AGA | CAG | CCA | GCA | ACA | GTG | 3840 |
| Leu | Glu | Glu | Ser | Cys | Ala | Cys | Cys | Arg | Gln | Arg | Gln | Pro | Ala | Thr | Val | |
| 1265 | | | | 1270 | | | | | 1275 | | | | | | 1280 | |
| CCA | GAG | CTG | CAG | AAC | GCA | GCT | CTG | CTC | TGC | GGG | AGG | AGG | TGC | AGA | GCC | 3888 |
| Pro | Glu | Leu | Gln | Asn | Ala | Ala | Leu | Leu | Cys | Gly | Arg | Arg | Cys | Arg | Ala | |
| | | | 1285 | | | | | 1290 | | | | | 1295 | | | |
| TCC | GGG | AGG | GAG | GCT | GAG | AAA | CAG | CGG | GTG | GCT | TCA | GAG | AAC | CTG | CGG | 3936 |
| Ser | Gly | Arg | Glu | Ala | Glu | Lys | Gln | Arg | Val | Ala | Ser | Glu | Asn | Leu | Arg | |
| | | | 1300 | | | | | 1305 | | | | | 1310 | | | |
| CAG | GAG | CTG | ACC | TCA | CAG | GCT | GAG | CGT | GCG | GAG | GAG | CTG | GGC | CAA | GAA | 3984 |
| Gln | Glu | Leu | Thr | Ser | Gln | Ala | Glu | Arg | Ala | Glu | Glu | Leu | Gly | Gln | Glu | |
| | | | 1315 | | | | | 1320 | | | | | 1325 | | | |
| TTG | AAG | GCG | TGG | CAG | GAG | AAG | TTC | TTC | CAG | AAA | GAG | CAG | GCC | CTC | TCC | 4032 |
| Leu | Lys | Ala | Trp | Gln | Glu | Lys | Phe | Phe | Gln | Lys | Glu | Gln | Ala | Leu | Ser | |
| | | | 1330 | | | | | 1335 | | | | | 1340 | | | |
| ACC | CTG | CAG | CTC | GAG | CAC | ACC | AGC | ACA | CAG | GCC | CTG | GTG | AGT | GAG | CTG | 4080 |
| Thr | Leu | Gln | Leu | Glu | His | Thr | Ser | Thr | Gln | Ala | Leu | Val | Ser | Glu | Leu | |
| 1345 | | | | 1350 | | | | | 1355 | | | | | | 1360 | |
| CTG | CCA | GCT | AAG | CAC | CTC | TGC | CAG | CAG | CTG | CAG | GCC | GAG | CAG | GCC | GCT | 4128 |
| Leu | Pro | Ala | Lys | His | Leu | Cys | Gln | Gln | Leu | Gln | Ala | Glu | Gln | Ala | Ala | |
| | | | | 1365 | | | | | 1370 | | | | | 1375 | | |
| GCC | GAG | AAA | CGC | CAC | CGT | GAG | GAG | CTG | GAG | CAG | AGC | AAG | CAG | GCC | GCT | 4176 |
| Ala | Glu | Lys | Arg | His | Arg | Glu | Glu | Leu | Glu | Gln | Ser | Lys | Gln | Ala | Ala | |
| | | | 1380 | | | | | 1385 | | | | | 1390 | | | |
| GGG | GGA | CTG | CGG | GCA | GAG | CTG | CTG | CGG | GCC | CAG | CGG | GAG | CTT | GGG | GAG | 4224 |
| Gly | Gly | Leu | Arg | Ala | Glu | Leu | Leu | Arg | Ala | Gln | Arg | Glu | Leu | Gly | Glu | |
| | | | 1395 | | | | | 1400 | | | | | 1405 | | | |
| CTG | ATT | CCT | CTG | CGG | CAG | AAG | GTG | GCA | GAG | CAG | GAG | CGA | ACA | GCT | CAG | 4272 |
| Leu | Ile | Pro | Leu | Arg | Gln | Lys | Val | Ala | Glu | Gln | Glu | Arg | Thr | Ala | Gln | |
| | | | 1410 | | | | | 1415 | | | | | 1420 | | | |
| CAG | CTG | CGG | GCA | GAG | AAG | GCC | AGC | TAT | GCA | GAG | CAG | CTG | AGC | ATG | CTG | 4320 |
| Gln | Leu | Arg | Ala | Glu | Lys | Ala | Ser | Tyr | Ala | Glu | Gln | Leu | Ser | Met | Leu | |
| 1425 | | | | 1430 | | | | | 1435 | | | | | | 1440 | |
| AAG | AAG | GCG | CAT | GGC | CTG | CTG | GCA | GAG | GAG | AAC | CGG | GGG | CTG | GGT | GAG | 4368 |
| Lys | Lys | Ala | His | Gly | Leu | Leu | Ala | Glu | Glu | Asn | Arg | Gly | Leu | Gly | Glu | |
| | | | | 1445 | | | | | 1450 | | | | | 1455 | | |
| CGG | GCC | AAC | CTT | GGC | CGG | CAG | TTT | CTG | GAA | GTG | GAG | TTG | GAC | CAG | GCC | 4416 |
| Arg | Ala | Asn | Leu | Gly | Arg | Gln | Phe | Leu | Glu | Val | Glu | Leu | Asp | Gln | Ala | |
| | | | | 1460 | | | | | 1465 | | | | | 1470 | | |
| CGG | GAA | AAG | TAT | GTC | CAA | GAG | TTG | GCA | GCC | GTA | CGT | GCT | GAT | GCT | GAG | 4464 |
| Arg | Glu | Lys | Tyr | Val | Gln | Glu | Leu | Ala | Ala | Val | Arg | Ala | Asp | Ala | Glu | |
| | | | 1475 | | | | | 1480 | | | | | 1485 | | | |
| ACC | CGT | CTG | GCT | GAG | GTG | CAG | CGA | GAA | GCA | CAG | AGC | ACT | GCC | CGG | GAG | 4512 |
| Thr | Arg | Leu | Ala | Glu | Val | Gln | Arg | Glu | Ala | Gln | Ser | Thr | Ala | Arg | Glu | |
| | | | 1490 | | | | | 1495 | | | | | 1500 | | | |
| CTG | GAG | GTG | ATG | ACT | GCC | AAG | TAT | GAG | GGT | GCC | AAG | GTC | AAG | GTC | CTG | 4560 |
| Leu | Glu | Val | Met | Thr | Ala | Lys | Tyr | Glu | Gly | Ala | Lys | Val | Lys | Val | Leu | |
| 1505 | | | | 1510 | | | | | 1515 | | | | | | 1520 | |
| GAG | GAG | AGG | CAG | CGG | TTC | CAG | GAA | GAG | AGG | CAG | AAA | CTC | ACT | GCC | CAG | 4608 |
| Glu | Glu | Arg | Gln | Arg | Phe | Gln | Glu | Glu | Arg | Gln | Lys | Leu | Thr | Ala | Gln | |
| | | | | 1525 | | | | | 1530 | | | | | 1535 | | |
| GTG | GAA | GAA | CTG | AGT | AAG | AAA | CTG | GCT | GAC | TCT | GAC | CAA | GCC | AGC | AAG | 4656 |
| Val | Glu | Glu | Leu | Ser | Lys | Lys | Leu | Ala | Asp | Ser | Asp | Gln | Ala | Ser | Lys | |
| | | | | 1540 | | | | | 1545 | | | | | 1550 | | |
| GTG | CAG | CAG | CAG | AAG | CTG | AAG | GCT | GTC | CAG | GCT | CAG | GGA | GGC | GAG | AGC | 4704 |
| Val | Gln | Gln | Gln | Lys | Leu | Lys | Ala | Val | Gln | Ala | Gln | Gly | Gly | Glu | Ser | |
| | | | | 1555 | | | | | 1560 | | | | | 1565 | | |
| CAG | CAG | GAG | GCC | CAG | CGC | TTC | CAG | GCC | CAG | CTG | AAT | GAA | CTG | CAA | GCC | 4752 |
| Gln | Gln | Glu | Ala | Gln | Arg | Phe | Gln | Ala | Gln | Leu | Asn | Glu | Leu | Gln | Ala | |
| | | | | 1570 | | | | | 1575 | | | | | 1580 | | |

```
CAG TTG AGC CAG AAG GAG CAG GCA GCT GAG CAC TAT AAG CTG CAG ATG          4800
Gln Leu Ser Gln Lys Glu Gln Ala Ala Glu His Tyr Lys Leu Gln Met
1585            1590            1595            1600

GAG AAA GCC AAA ACA CAT TAT GAT GCC AAG AAG CAG CAG AAC CAA GAG          4848
Glu Lys Ala Lys Thr His Tyr Asp Ala Lys Lys Gln Gln Asn Gln Glu
                1605            1610            1615

CTG CAG GAG CAG CTG CGG AGC CTG GAG CAG CTG CAG AAG GAA AAC AAA          4896
Leu Gln Glu Gln Leu Arg Ser Leu Glu Gln Leu Gln Lys Glu Asn Lys
        1620            1625            1630

GAG CTG CGA GCT GAA GCT GAA CGG CTG GGC CAT GAG CTA CAG CAG GCT          4944
Glu Leu Arg Ala Glu Ala Glu Arg Leu Gly His Glu Leu Gln Gln Ala
        1635            1640            1645

GGG CTG AAG ACC AAG GAG GCT GAA CAG ACC TGC CGC CAC CTT ACT GCC          4992
Gly Leu Lys Thr Lys Glu Ala Glu Gln Thr Cys Arg His Leu Thr Ala
1650            1655            1660

CAG GTG CGC AGC CTG GAG GCA CAG GTT GCC CAT GCA GAC CAG CAG CTT          5040
Gln Val Arg Ser Leu Glu Ala Gln Val Ala His Ala Asp Gln Gln Leu
1665            1670            1675            1680

CGA GAC CTG GGC AAA TTC CAG GTG GCA ACT GAT GCT TTA AAG AGC CGT          5088
Arg Asp Leu Gly Lys Phe Gln Val Ala Thr Asp Ala Leu Lys Ser Arg
        1685            1690            1695

GAG CCC CAG GCT AAG CCC CAG CTG GAC TTG AGT ATT GAC AGC CTG GAT          5136
Glu Pro Gln Ala Lys Pro Gln Leu Asp Leu Ser Ile Asp Ser Leu Asp
        1700            1705            1710

CTG AGC TGC GAG GAG GGG ACC CCA CTC AGT ATC ACC AGC AAG CTG CCT          5184
Leu Ser Cys Glu Glu Gly Thr Pro Leu Ser Ile Thr Ser Lys Leu Pro
        1715            1720            1725

CGT ACC CAG CCA GAC GGC ACC AGC GTC CCT GGA GAA CCA GCC TCA CCT          5232
Arg Thr Gln Pro Asp Gly Thr Ser Val Pro Gly Glu Pro Ala Ser Pro
1730            1735            1740

ATC TCC CAG CGC CTG CCC CCC AAG GTA GAA TCC CTG GAG AGT CTC TAC          5280
Ile Ser Gln Arg Leu Pro Pro Lys Val Glu Ser Leu Glu Ser Leu Tyr
1745            1750            1755            1760

TTC ACT CCC ATC CCT GCT CGG AGT CAG GCC CCC CTG GAG AGC AGC CTG          5328
Phe Thr Pro Ile Pro Ala Arg Ser Gln Ala Pro Leu Glu Ser Ser Leu
        1765            1770            1775

GAC TCC CTG GGA GAC GTC TTC CTG GAC TCG GGT CGT AAG ACC CGC TCC          5376
Asp Ser Leu Gly Asp Val Phe Leu Asp Ser Gly Arg Lys Thr Arg Ser
        1780            1785            1790

GCT CGT CGG CGC ACC ACG CAG ATC ATC AAC ATC ACC ATG ACC AAG AAG          5424
Ala Arg Arg Arg Thr Thr Gln Ile Ile Asn Ile Thr Met Thr Lys Lys
        1795            1800            1805

CTA GAT GTG GAA GAG CCA GAC AGC GCC AAC TCA TCG TTC TAC AGC ACG          5472
Leu Asp Val Glu Glu Pro Asp Ser Ala Asn Ser Ser Phe Tyr Ser Thr
1810            1815            1820

CGG TCT GCT CCT GCT TCC CAG GCT AGC CTG CGA GCC ACC TCC TCT ACT          5520
Arg Ser Ala Pro Ala Ser Gln Ala Ser Leu Arg Ala Thr Ser Ser Thr
1825            1830            1835            1840

CAG TCT CTA GCT CGC CTG GGT TCT CCC GAT TAT GGC AAC TCA GCC CTG          5568
Gln Ser Leu Ala Arg Leu Gly Ser Pro Asp Tyr Gly Asn Ser Ala Leu
        1845            1850            1855

CTC AGC TTG CCT GGC TAC CGC CCC ACC ACT CGC AGT CTT GCT CGT CGT          5616
Leu Ser Leu Pro Gly Tyr Arg Pro Thr Thr Arg Ser Ser Ala Arg Arg
        1860            1865            1870

TCC CAG GCC GGG GTG TCC AGT GGG GCC CCT CCA GGA AGG AAC AGC TTC          5664
Ser Gln Ala Gly Val Ser Ser Gly Ala Pro Pro Gly Arg Asn Ser Phe
        1875            1880            1885

TAC ATG GGC ACT TGC CAG GAT GAG CCT GAG CAG CTG GAT GAC TGG AAC          5712
Tyr Met Gly Thr Cys Gln Asp Glu Pro Glu Gln Leu Asp Asp Trp Asn
1890            1895            1900
```

| | | | | | | | | | | | | | | | | |
|---|---|---|---|---|---|---|---|---|---|---|---|---|---|---|---|---|
| CGC | ATT | GCA | GAG | CTG | CAG | CAG | CGC | AAT | CGA | GTG | TGC | CCC | CCA | CAT | CTG | 5760 |
| Arg | Ile | Ala | Glu | Leu | Gln | Gln | Arg | Asn | Arg | Val | Cys | Pro | Pro | His | Leu | |
| 1905 | | | | 1910 | | | | | 1915 | | | | | | 1920 | |
| AAG | ACC | TGC | TAT | CCC | CTG | GAG | TCC | AGG | CCT | TCC | CTG | AGC | CTG | GGC | ACC | 5808 |
| Lys | Thr | Cys | Tyr | Pro | Leu | Glu | Ser | Arg | Pro | Ser | Leu | Ser | Leu | Gly | Thr | |
| | | | | 1925 | | | | | 1930 | | | | | | 1935 | |
| ATC | ACA | GAT | GAG | GAG | ATG | AAA | ACT | GGA | GAC | CCC | CAA | GAG | ACC | CTG | CGC | 5856 |
| Ile | Thr | Asp | Glu | Glu | Met | Lys | Thr | Gly | Asp | Pro | Gln | Glu | Thr | Leu | Arg | |
| | | | | 1940 | | | | | 1945 | | | | | | 1950 | |
| CGA | GCC | AGC | ATG | CAG | CCA | ATC | CAG | ATA | GCC | GAG | GGC | ACT | GGC | ATC | ACC | 5904 |
| Arg | Ala | Ser | Met | Gln | Pro | Ile | Gln | Ile | Ala | Glu | Gly | Thr | Gly | Ile | Thr | |
| | | | 1955 | | | | | 1960 | | | | | 1965 | | | |
| ACC | CGG | CAG | CAG | CGC | AAA | CGG | GTC | TCC | CTA | GAG | CCC | CAC | CAG | GGC | CCT | 5952 |
| Thr | Arg | Gln | Gln | Arg | Lys | Arg | Val | Ser | Leu | Glu | Pro | His | Gln | Gly | Pro | |
| | 1970 | | | | | 1975 | | | | | 1980 | | | | | |
| GGA | ACT | CCT | GAG | TCT | AAG | AAG | GCC | ACC | AGC | TGT | TTC | CCA | CGC | CCC | ATG | 6000 |
| Gly | Thr | Pro | Glu | Ser | Lys | Lys | Ala | Thr | Ser | Cys | Phe | Pro | Arg | Pro | Met | |
| 1985 | | | | | 1990 | | | | | 1995 | | | | | 2000 | |
| ACT | CCC | CGA | GAC | CGA | CAT | GAA | GGG | CGC | AAA | CAG | AGC | ACT | ACT | GAG | GCC | 6048 |
| Thr | Pro | Arg | Asp | Arg | His | Glu | Gly | Arg | Lys | Gln | Ser | Thr | Thr | Glu | Ala | |
| | | | | 2005 | | | | | 2010 | | | | | | 2015 | |
| CAG | AAG | AAA | GCA | GCT | CCA | GCT | TCT | ACT | AAA | CAG | GCT | GAC | CGG | CGC | CAG | 6096 |
| Gln | Lys | Lys | Ala | Ala | Pro | Ala | Ser | Thr | Lys | Gln | Ala | Asp | Arg | Arg | Gln | |
| | | | | 2020 | | | | | 2025 | | | | | | 2030 | |
| TCG | ATG | GCC | TTC | AGC | ATC | CTC | AAC | ACA | CCC | AAG | AAG | CTA | GGG | AAC | AGC | 6144 |
| Ser | Met | Ala | Phe | Ser | Ile | Leu | Asn | Thr | Pro | Lys | Lys | Leu | Gly | Asn | Ser | |
| | | | 2035 | | | | | 2040 | | | | | 2045 | | | |
| CTT | CTG | CGG | CGG | GGA | GCC | TCA | AAG | AAG | GCC | CTG | TCC | AAG | GCT | TCC | CCC | 6192 |
| Leu | Leu | Arg | Arg | Gly | Ala | Ser | Lys | Lys | Ala | Leu | Ser | Lys | Ala | Ser | Pro | |
| | 2050 | | | | | 2055 | | | | | 2060 | | | | | |
| AAC | ACT | CGC | AGT | GGA | ACC | CGC | CGT | TCT | CCG | CGC | ATT | GCC | ACC | ACC | ACA | 6240 |
| Asn | Thr | Arg | Ser | Gly | Thr | Arg | Arg | Ser | Pro | Arg | Ile | Ala | Thr | Thr | Thr | |
| 2065 | | | | | 2070 | | | | | 2075 | | | | | 2080 | |
| GCC | AGT | GCC | GCC | ACT | GCT | GCC | GCC | ATT | GGT | GCC | ACC | CCT | CGA | GCC | AAG | 6288 |
| Ala | Ser | Ala | Ala | Thr | Ala | Ala | Ala | Ile | Gly | Ala | Thr | Pro | Arg | Ala | Lys | |
| | | | | 2085 | | | | | 2090 | | | | | | 2095 | |
| GGC | AAG | GCA | AAG | CAC | TAA | | | | | | | | | | | 6306 |
| Gly | Lys | Ala | Lys | His | | | | | | | | | | | | |
| | | | | 2100 | | | | | | | | | | | | |

( 2 ) INFORMATION FOR SEQ ID NO:4:

( i ) SEQUENCE CHARACTERISTICS:
        ( A ) LENGTH: 2101 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Thr | Leu | His | Ala | Thr | Arg | Gly | Ala | Ala | Leu | Leu | Ser | Trp | Val | Asn |
| 1 | | | | 5 | | | | | 10 | | | | | 15 | |
| Ser | Leu | His | Val | Ala | Asp | Pro | Val | Glu | Ala | Val | Leu | Gln | Leu | Gln | Asp |
| | | | | 20 | | | | | 25 | | | | | 30 | |
| Cys | Ser | Ile | Phe | Ile | Lys | Ile | Ile | Asp | Arg | Ile | His | Gly | Thr | Glu | Glu |
| | | | 35 | | | | | 40 | | | | | 45 | | |
| Gly | Gln | Gln | Ile | Leu | Lys | Gln | Pro | Val | Ser | Glu | Arg | Leu | Asp | Phe | Val |
| | | 50 | | | | | 55 | | | | | 60 | | | |
| Cys | Ser | Phe | Leu | Gln | Lys | Asn | Arg | Lys | His | Pro | Ser | Ser | Pro | Glu | Cys |
| 65 | | | | | 70 | | | | | 75 | | | | | 80 |
| Leu | Val | Ser | Ala | Gln | Lys | Val | Leu | Glu | Gly | Ser | Glu | Leu | Glu | Leu | Ala |

|     |     |     |     |     | 85  |     |     |     |     | 90  |     |     |     |     | 95  |     |     |
| --- | --- | --- | --- | --- | --- | --- | --- | --- | --- | --- | --- | --- | --- | --- | --- | --- | --- |

Lys Met Thr Met Leu Leu Leu Tyr His Ser Thr Met Ser Ser Lys Ser
                100                 105                 110

Pro Arg Asp Trp Glu Gln Phe Glu Tyr Lys Ile Gln Ala Glu Leu Ala
        115                 120                 125

Val Ile Leu Lys Phe Val Leu Asp His Glu Asp Gly Leu Asn Leu Asn
    130                 135                 140

Glu Asp Leu Glu Asn Phe Leu Gln Lys Ala Pro Val Pro Ser Thr Cys
145                 150                 155                 160

Ser Ser Thr Phe Pro Glu Glu Leu Ser Pro Pro Ser His Gln Ala Lys
                165                 170                 175

Arg Glu Ile Arg Phe Leu Glu Leu Gln Lys Val Ala Ser Ser Ser Ser
            180                 185                 190

Gly Asn Asn Phe Leu Ser Gly Ser Pro Ala Ser Pro Met Gly Asp Ile
        195                 200                 205

Leu Gln Thr Pro Gln Phe Gln Met Arg Arg Leu Lys Lys Gln Leu Ala
    210                 215                 220

Asp Glu Arg Ser Asn Arg Asp Glu Leu Glu Leu Glu Leu Ala Glu Asn
225                 230                 235                 240

Arg Lys Leu Leu Thr Glu Lys Asp Ala Gln Ile Ala Met Met Gln Gln
                245                 250                 255

Arg Ile Asp Arg Leu Ala Leu Leu Asn Glu Lys Gln Ala Ala Ser Pro
            260                 265                 270

Leu Glu Pro Lys Glu Leu Glu Glu Leu Arg Asp Lys Asn Glu Ser Leu
        275                 280                 285

Thr Met Arg Leu His Glu Thr Leu Lys Gln Cys Gln Asp Leu Lys Thr
290                 295                 300

Glu Lys Ser Gln Met Asp Arg Lys Ile Asn Gln Leu Ser Glu Glu Asn
305                 310                 315                 320

Gly Asp Leu Ser Phe Lys Leu Arg Glu Phe Ala Ser His Leu Gln Gln
                325                 330                 335

Leu Gln Asp Ala Leu Asn Glu Leu Thr Glu Glu His Ser Lys Ala Thr
            340                 345                 350

Gln Glu Trp Leu Glu Lys Gln Ala Gln Leu Glu Lys Glu Leu Ser Ala
        355                 360                 365

Ala Leu Gln Asp Lys Lys Cys Leu Glu Glu Lys Asn Glu Ile Leu Gln
370                 375                 380

Gly Lys Leu Ser Gln Leu Glu Glu His Leu Ser Gln Leu Gln Asp Asn
385                 390                 395                 400

Pro Pro Gln Glu Lys Gly Glu Val Leu Gly Asp Val Leu Gln Leu Glu
                405                 410                 415

Thr Leu Lys Gln Glu Ala Ala Thr Leu Ala Ala Asn Asn Thr Gln Leu
            420                 425                 430

Gln Ala Arg Val Glu Met Leu Glu Thr Glu Arg Gly Gln Gln Glu Ala
        435                 440                 445

Lys Leu Leu Ala Glu Arg Gly His Phe Glu Glu Glu Lys Gln Gln Leu
450                 455                 460

Ser Ser Leu Ile Thr Asp Leu Gln Ser Ser Ile Ser Asn Leu Ser Gln
465                 470                 475                 480

Ala Lys Glu Glu Leu Glu Gln Ala Ser Gln Ala His Gly Ala Arg Leu
                485                 490                 495

Thr Ala Gln Val Ala Ser Leu Thr Ser Glu Leu Thr Thr Leu Asn Ala
            500                 505                 510

```
Thr Ile Gln Gln Gln Asp Gln Glu Leu Ala Gly Leu Lys Gln Gln Ala
        515             520                     525

Lys Glu Lys Gln Ala Gln Leu Ala Gln Thr Leu Gln Gln Gln Glu Gln
    530             535                     540

Ala Ser Gln Gly Leu Arg His Gln Val Glu Gln Leu Ser Ser Ser Leu
545             550                 555                     560

Lys Gln Lys Glu Gln Gln Leu Lys Glu Val Ala Glu Lys Gln Glu Ala
                565             570             575

Thr Arg Gln Asp His Ala Gln Gln Leu Ala Thr Ala Ala Glu Glu Arg
            580             585                 590

Glu Ala Ser Leu Arg Glu Arg Asp Ala Ala Leu Lys Gln Leu Glu Ala
        595             600                 605

Leu Glu Lys Glu Lys Ala Ala Lys Leu Glu Ile Leu Gln Gln Gln Leu
    610             615                 620

Gln Val Ala Asn Glu Ala Arg Asp Ser Ala Gln Thr Ser Val Thr Gln
625             630                 635                     640

Ala Gln Arg Glu Lys Ala Glu Leu Ser Arg Lys Val Glu Glu Leu Gln
                645             650                 655

Ala Cys Val Glu Thr Ala Arg Gln Glu Gln His Glu Ala Gln Ala Gln
            660             665                 670

Val Ala Glu Leu Glu Leu Gln Leu Arg Ser Glu Gln Gln Lys Ala Thr
        675             680                 685

Glu Lys Glu Arg Val Ala Gln Glu Lys Asp Gln Leu Gln Glu Gln Leu
    690             695                 700

Gln Ala Leu Lys Glu Ser Leu Lys Val Thr Lys Gly Ser Leu Glu Glu
705             710                 715                     720

Glu Lys Arg Arg Ala Ala Asp Ala Leu Glu Glu Gln Gln Arg Cys Ile
                725             730                 735

Ser Glu Leu Lys Ala Glu Thr Arg Ser Leu Val Glu Gln His Lys Arg
            740             745                 750

Glu Arg Lys Glu Leu Glu Glu Glu Arg Ala Gly Arg Lys Gly Leu Glu
    755             760                 765

Ala Arg Leu Leu Gln Leu Gly Glu Ala His Gln Ala Glu Thr Glu Val
770             775                 780

Leu Arg Arg Glu Leu Ala Glu Ala Met Ala Ala Gln His Thr Ala Glu
785             790             795                         800

Ser Glu Cys Glu Gln Leu Val Lys Glu Val Ala Ala Trp Arg Asp Gly
                805             810                 815

Tyr Glu Asp Ser Gln Gln Glu Glu Ala Gln Tyr Gly Ala Met Phe Gln
            820             825                 830

Glu Gln Leu Met Thr Leu Lys Glu Glu Cys Glu Lys Ala Arg Gln Glu
    835             840             845

Leu Gln Glu Ala Lys Glu Lys Val Ala Gly Ile Glu Ser His Ser Glu
    850             855             860

Leu Gln Ile Ser Arg Gln Gln Asn Lys Leu Ala Glu Leu His Ala Asn
865             870             875                         880

Leu Ala Arg Ala Leu Gln Gln Val Gln Glu Lys Glu Val Arg Ala Gln
            885             890                 895

Lys Leu Ala Asp Asp Leu Ser Thr Leu Gln Glu Lys Met Ala Ala Thr
            900             905                 910

Ser Lys Glu Val Ala Arg Leu Glu Thr Leu Val Arg Lys Ala Gly Glu
    915             920                 925

Gln Gln Glu Thr Ala Ser Arg Glu Leu Val Lys Glu Pro Ala Arg Ala
930             935                 940
```

```
Gly Asp Arg Gln Pro Glu Trp Leu Glu Glu Gln Gly Arg Gln Phe
945                 950                 955                 960

Cys Ser Thr Gln Ala Ala Leu Gln Ala Met Glu Arg Glu Ala Glu Gln
                965                 970                 975

Met Gly Asn Glu Leu Glu Arg Leu Arg Ala Ala Leu Met Glu Ser Gln
            980                 985                 990

Gly Gln Gln Gln Glu Glu Arg Gly Gln Gln Glu Arg Glu Val Ala Arg
        995                 1000                1005

Leu Thr Gln Glu Arg Gly Arg Ala Gln Ala Asp Leu Ala Leu Glu Lys
    1010                1015                1020

Ala Ala Arg Ala Glu Leu Glu Met Arg Leu Gln Asn Ala Leu Asn Glu
1025                1030                1035                1040

Gln Arg Val Glu Phe Ala Thr Leu Gln Glu Ala Leu Ala His Ala Leu
                1045                1050                1055

Thr Glu Lys Glu Gly Lys Asp Gln Glu Leu Ala Lys Leu Arg Gly Leu
            1060                1065                1070

Glu Ala Ala Gln Ile Lys Glu Leu Glu Glu Leu Arg Gln Thr Val Lys
        1075                1080                1085

Gln Leu Lys Glu Gln Leu Ala Lys Lys Glu Lys Glu His Ala Ser Gly
1090                1095                1100

Ser Gly Ala Gln Ser Glu Ala Ala Gly Arg Thr Glu Pro Thr Gly Pro
1105                1110                1115                1120

Lys Leu Glu Ala Leu Arg Ala Glu Val Ser Lys Leu Glu Gln Gln Cys
                1125                1130                1135

Gln Lys Gln Gln Glu Gln Ala Asp Ser Leu Glu Arg Ser Leu Glu Ala
            1140                1145                1150

Glu Arg Ala Ser Arg Ala Glu Arg Asp Ser Ala Leu Glu Thr Leu Gln
        1155                1160                1165

Gly Gln Leu Glu Glu Lys Ala Gln Glu Leu Gly His Ser Gln Ser Ala
    1170                1175                1180

Leu Ala Ser Ala Gln Arg Glu Leu Ala Ala Phe Arg Thr Lys Val Gln
1185                1190                1195                1200

Asp His Ser Lys Ala Glu Asp Glu Trp Lys Ala Gln Val Ala Arg Gly
                1205                1210                1215

Arg Gln Glu Ala Glu Arg Lys Asn Ser Leu Ile Ser Ser Leu Glu Glu
            1220                1225                1230

Glu Val Ser Ile Leu Asn Arg Gln Val Leu Glu Lys Glu Gly Glu Ser
        1235                1240                1245

Lys Glu Leu Lys Arg Leu Val Met Ala Glu Ser Glu Lys Ser Gln Lys
    1250                1255                1260

Leu Glu Glu Ser Cys Ala Cys Cys Arg Gln Arg Gln Pro Ala Thr Val
1265                1270                1275                1280

Pro Glu Leu Gln Asn Ala Ala Leu Leu Cys Gly Arg Arg Cys Arg Ala
                1285                1290                1295

Ser Gly Arg Glu Ala Glu Lys Gln Arg Val Ala Ser Glu Asn Leu Arg
            1300                1305                1310

Gln Glu Leu Thr Ser Gln Ala Glu Arg Ala Glu Glu Leu Gly Gln Glu
        1315                1320                1325

Leu Lys Ala Trp Gln Glu Lys Phe Phe Gln Lys Glu Gln Ala Leu Ser
    1330                1335                1340

Thr Leu Gln Leu Glu His Thr Ser Thr Gln Ala Leu Val Ser Glu Leu
1345                1350                1355                1360

Leu Pro Ala Lys His Leu Cys Gln Gln Leu Gln Ala Glu Gln Ala Ala
```

-continued

```
                    1365                      1370                      1375
Ala Glu Lys Arg His Arg Glu Glu Leu Glu Gln Ser Lys Gln Ala Ala
            1380                      1385                      1390
Gly Gly Leu Arg Ala Glu Leu Leu Arg Ala Gln Arg Glu Leu Gly Glu
            1395                      1400                      1405
Leu Ile Pro Leu Arg Gln Lys Val Ala Glu Gln Glu Arg Thr Ala Gln
    1410                      1415                      1420
Gln Leu Arg Ala Glu Lys Ala Ser Tyr Ala Glu Gln Leu Ser Met Leu
1425                      1430                      1435                      1440
Lys Lys Ala His Gly Leu Leu Ala Glu Glu Asn Arg Gly Leu Gly Glu
            1445                      1450                      1455
Arg Ala Asn Leu Gly Arg Gln Phe Leu Glu Val Glu Leu Asp Gln Ala
            1460                      1465                      1470
Arg Glu Lys Tyr Val Gln Glu Leu Ala Ala Val Arg Ala Asp Ala Glu
            1475                      1480                      1485
Thr Arg Leu Ala Glu Val Gln Arg Glu Ala Gln Ser Thr Ala Arg Glu
            1490                      1495                      1500
Leu Glu Val Met Thr Ala Lys Tyr Glu Gly Ala Lys Val Lys Val Leu
    1505                      1510                      1515                      1520
Glu Glu Arg Gln Arg Phe Gln Glu Glu Arg Gln Lys Leu Thr Ala Gln
            1525                      1530                      1535
Val Glu Glu Leu Ser Lys Lys Leu Ala Asp Ser Asp Gln Ala Ser Lys
            1540                      1545                      1550
Val Gln Gln Gln Lys Leu Lys Ala Val Gln Ala Gln Gly Gly Glu Ser
            1555                      1560                      1565
Gln Gln Glu Ala Gln Arg Phe Gln Ala Gln Leu Asn Glu Leu Gln Ala
            1570                      1575                      1580
Gln Leu Ser Gln Lys Glu Gln Ala Ala Glu His Tyr Lys Leu Gln Met
    1585                      1590                      1595                      1600
Glu Lys Ala Lys Thr His Tyr Asp Ala Lys Lys Gln Gln Asn Gln Glu
            1605                      1610                      1615
Leu Gln Glu Gln Leu Arg Ser Leu Glu Gln Leu Gln Lys Glu Asn Lys
            1620                      1625                      1630
Glu Leu Arg Ala Glu Ala Glu Arg Leu Gly His Glu Leu Gln Gln Ala
            1635                      1640                      1645
Gly Leu Lys Thr Lys Glu Ala Glu Gln Thr Cys Arg His Leu Thr Ala
            1650                      1655                      1660
Gln Val Arg Ser Leu Glu Ala Gln Val Ala His Ala Asp Gln Gln Leu
    1665                      1670                      1675                      1680
Arg Asp Leu Gly Lys Phe Gln Val Ala Thr Asp Ala Leu Lys Ser Arg
                                      1685                      1690                      1695
Glu Pro Gln Ala Lys Pro Gln Leu Asp Leu Ser Ile Asp Ser Leu Asp
            1700                      1705                      1710
Leu Ser Cys Glu Glu Gly Thr Pro Leu Ser Ile Thr Ser Lys Leu Pro
            1715                      1720                      1725
Arg Thr Gln Pro Asp Gly Thr Ser Val Pro Gly Glu Pro Ala Ser Pro
            1730                      1735                      1740
Ile Ser Gln Arg Leu Pro Pro Lys Val Glu Ser Leu Glu Ser Leu Tyr
1745                      1750                      1755                      1760
Phe Thr Pro Ile Pro Ala Arg Ser Gln Ala Pro Leu Glu Ser Ser Leu
            1765                      1770                      1775
Asp Ser Leu Gly Asp Val Phe Leu Asp Ser Gly Arg Lys Thr Arg Ser
            1780                      1785                      1790
```

Ala Arg Arg Arg Thr Thr Gln Ile Ile Asn Ile Thr Met Thr Lys Lys
1795                1800                1805

Leu Asp Val Glu Glu Pro Asp Ser Ala Asn Ser Ser Phe Tyr Ser Thr
1810                1815                1820

Arg Ser Ala Pro Ala Ser Gln Ala Ser Leu Arg Ala Thr Ser Ser Thr
1825            1830                1835                1840

Gln Ser Leu Ala Arg Leu Gly Ser Pro Asp Tyr Gly Asn Ser Ala Leu
                1845                1850                1855

Leu Ser Leu Pro Gly Tyr Arg Pro Thr Thr Arg Ser Ser Ala Arg Arg
1860                1865                1870

Ser Gln Ala Gly Val Ser Ser Gly Ala Pro Pro Gly Arg Asn Ser Phe
1875                1880                1885

Tyr Met Gly Thr Cys Gln Asp Glu Pro Glu Gln Leu Asp Asp Trp Asn
    1890            1895            1900

Arg Ile Ala Glu Leu Gln Gln Arg Asn Arg Val Cys Pro Pro His Leu
1905                1910                1915                1920

Lys Thr Cys Tyr Pro Leu Glu Ser Arg Pro Ser Leu Ser Leu Gly Thr
                1925                1930                1935

Ile Thr Asp Glu Glu Met Lys Thr Gly Asp Pro Gln Glu Thr Leu Arg
            1940            1945            1950

Arg Ala Ser Met Gln Pro Ile Gln Ile Ala Glu Gly Thr Gly Ile Thr
        1955                1960                1965

Thr Arg Gln Gln Arg Lys Arg Val Ser Leu Glu Pro His Gln Gly Pro
    1970            1975            1980

Gly Thr Pro Glu Ser Lys Lys Ala Thr Ser Cys Phe Pro Arg Pro Met
1985            1990            1995            2000

Thr Pro Arg Asp Arg His Glu Gly Arg Lys Gln Ser Thr Thr Glu Ala
            2005            2010            2015

Gln Lys Lys Ala Ala Pro Ala Ser Thr Lys Gln Ala Asp Arg Arg Gln
            2020            2025            2030

Ser Met Ala Phe Ser Ile Leu Asn Thr Pro Lys Lys Leu Gly Asn Ser
        2035            2040            2045

Leu Leu Arg Arg Gly Ala Ser Lys Lys Ala Leu Ser Lys Ala Ser Pro
2050            2055            2060

Asn Thr Arg Ser Gly Thr Arg Arg Ser Pro Arg Ile Ala Thr Thr Thr
2065            2070            2075            2080

Ala Ser Ala Ala Thr Ala Ala Ala Ile Gly Ala Thr Pro Arg Ala Lys
            2085            2090            2095

Gly Lys Ala Lys His
        2100

( 2 ) INFORMATION FOR SEQ ID NO:5:

( i ) SEQUENCE CHARACTERISTICS:
        ( A ) LENGTH: 353 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: mRNA
        ( B ) LOCATION: 1..353
        ( D ) OTHER INFORMATION: /note="ANTI-SENSE SEQUENCE TO PART
        OF THE MTI MRNA TRANSCRIPT: N TERMINUS OF PROTEIN
        CODING SEQUENCE AND UPSTREAM 53 NUCLEOTIDES"

( i x ) FEATURE:
        ( A ) NAME/KEY: misc_feature ( B ) LOCATION: 298..300
( D ) OTHER INFORMATION: /note="MT1 INITIATION CODON SEQUENCE ON COMPLEMENTARY STRAND"

( x i ) SEQUENCE DESCRIPTION: SEQ ID NO:5:

| | | | | | |
|---|---|---|---|---|---|
| CTCAATTTTA | ACTTGTTCTT | GTTTTCTCG | TTGTGCAAGG | CGAGCTGCAA | CTTCTTCAGG | 60 |
| TGGTCGCTCC | CTTATAGAAG | ATGAGGATGC | TTCTGAAAGT | GCAGGTGTGG | GTTTTCCTTC | 120 |
| ACCAATTTCA | GGGTGATCAG | TTTTTAAAGA | TTCCTCAGGC | TGAACTGCAG | GGGCTGGGAC | 180 |
| CGACAGGGTA | TCACCTGCTG | CAGAAATAAT | TTGAGCCGCT | TCTGTAGGTG | CTGTTGCTGA | 240 |
| AGCTGGAGTA | TCTCCCTTTT | GTTGTTGGAG | TTGTGAGGCA | GGCTGTTTAG | ATTCTTTCAT | 300 |
| TACTTCTGAT | ACACTAGAGA | TTTTAGTGG | ACCCGACTGA | ATCGATTTCT | TTG | 353 |

( 2 ) INFORMATION FOR SEQ ID NO:6:

( i ) SEQUENCE CHARACTERISTICS:
( A ) LENGTH: 348 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: mRNA
( B ) LOCATION: 1..348
( D ) OTHER INFORMATION: /note="ANTISENSE SEQUENCE TO PART OF MT2 TRANSCRIPT: N TERMINUS OF PROTEIN CODING REGION AND UPSTREAM 48 NUCLEOTIDE"

( i x ) FEATURE:
( A ) NAME/KEY: misc_feature
( B ) LOCATION: 298..300
( D ) OTHER INFORMATION: /note="MT2 INITIATION CODON SEQUENCE ON COMPLEMENTARY STRAND"

( x i ) SEQUENCE DESCRIPTION: SEQ ID NO:6:

| | | | | | |
|---|---|---|---|---|---|
| CATGGTCATC | TTCGCCAGTT | CCAGCTCTGA | TCCCTCTAGC | ACCTTCTGTG | CAGATACCAG | 60 |
| GCGTTCTGGG | GAAGAGGGAT | GTTTCGATT | TTTCTGCAGA | AAACTGCACA | CAAAGTCCAG | 120 |
| TCTCTCTGAC | ACCGGCTGCT | TCTTGATTTG | CTGTCCCTCT | TCAGTGCCAT | GGATTCTGTC | 180 |
| AATGATCTTG | ATGAAGATGC | TGCAGTCCTG | GAGCTGCAGC | ACAGCCTCCA | CAGGGTCAGC | 240 |
| CACGTGTAGA | CTGTTCACCC | AAGAGAGGAG | TGCAGCCCCC | CGGGTGGCGT | GGAGTGTCAT | 300 |
| CTTGGTGATG | CCAGACAGTC | ACTCCAATGC | GCCTGTAATC | CCAGCTAC | | 348 |

NOVEL MALIGNANT CELL TYPE MARKERS OF THE INTERIOR NUCLEAR MATRIX

This application is a divisional of U.S. Ser. No. 08/195,487 filed Feb. 14, 1994, which is a continuation of U.S. Ser. No. 07/901,701, filed Jun. 22, 1992, now abandoned.

REFERENCE TO RELATED APPLICATIONS

Related applications include: U.S. Ser. No. 08/195,487, filed Feb. 14, 1994, which is a continuation of U.S. Ser. No. 07/901,701, filed Jun. 22, 1992, now abandoned; U.S. Ser. No. 08/483,924, filed Jun. 7, 1995, which is a continuation of U.S. Ser. No. 08/195,487, filed Feb. 14, 1994, which is a continuation of U.S. Ser. No. 07/901,701, filed Jun. 22, 1992, now abandoned; U.S. Ser. No. 08/466,390, filed Jun. 6, 1995, which is a divisional of U.S. Ser. No. 08/195,487, filed Feb. 14, 1994, which is a continuation of U.S. Ser. No. 07/901,701, filed Jun. 22, 1992, now abandoned; U.S. Ser. No. 08/467,781, filed Jun. 6, 1995, which is a divisional of U.S. Ser. No. 08/195,487, filed Feb. 14, 1994, which is a continuation of U.S. Ser. No. 07/901,701, filed Jun. 22, 1992, now abandoned; U.S. Ser. No. 08/456,620, filed Jun. 1, 1995, which is a continuation of U.S. Ser. No. 08/112,646, filed Aug. 26, 1993, now abandoned, which is a continuation of U.S. Ser. No. 07/785,804, filed Oct. 31, 1991, now abandoned; U.S. Ser. No. 08/444,821, filed May 18, 1995, which is a divisional of U.S. Ser. No. 08/112,646, filed Aug. 26, 1993, now abandoned, which is a continuation of U.S. Ser. No. 07/785,804, filed Oct. 31, 1991, now abandoned; and U.S. Ser. No. 08/443,630, filed May 18, 1995, which is a divisional of U.S. Ser. No. 08/112,646, filed Aug. 26, 1993, now abandoned, which is a continuation of U.S. Ser. No. 07/785,804, filed Oct. 31, 1991, now abandoned.

BACKGROUND OF THE INVENTION

All eucaryotic cells, both plant and animal, have a nucleus surrounded by the cell cytoplasm. The nucleus contains the cellular DNA complexed with protein and termed chromatin. The chromatin, with its associated proteins, constitutes the major portion of the nuclear mass and is organized by the internal protein skeleton of the nucleus, referred to here as the nuclear matrix (NM). The nuclear matrix also is defined as the nuclear structure that remains following removal of the chromatin by digestion with DNase I and extraction with high salt. This skeletal nuclear structure further is characterized by the "interior nuclear matrix" (INM) and the bounding nuclear pore-lamina complex.

Diverse studies have implicated the NM in a wide variety of nuclear functions fundamental to the control of gene expression (For a general review see, for example, Fey et al. (1991) Crit. Rev. Euk. Gene Express 1:127–143). In particular, as described in U.S. Pat. Nos. 4,882,268 and 4,885,236, it is now known that certain nuclear matrix proteins, specifically interior nuclear matrix proteins, are useful as marker proteins for identifying cell types. For example, the presence and abundance of particular INM proteins have been shown to be characteristic of specific cell types and can be used to identify the tissue of origin of a cell or cell fragment present in a sample. One particularly important application of this discovery is the use of marker INM proteins in evaluating metastatic tissue. It is also known that the expression of certain INM proteins is altered in malignant or otherwise dysfunctional cells. The altered expression pattern of these proteins in malignant and/or dysfunctioning cells also makes the proteins and nucleic acids encoding the proteins useful as marker proteins, alone or in combination, for diagnostic purposes and for evaluating tissue viability. U.S. Pat. Nos. 4,882,628 and 4,885,236, issued Nov. 21, 1989 and Dec. 5, 1989, respectively, to Penman and Fey, disclose a method for selectively extracting insoluble INM proteins and their associated nucleic acids from cells or cellular debris and distinguishing the expression pattern of these proteins in a particular cell type by displaying the proteins on a two-dimensional electrophoresis gel. In addition, it recently has been discovered that INM proteins or protein fragments also may be released in soluble form from dying cells. (See PCT Publication WO93/09437, published May 13, 1993).

To date, molecular characterization of the specific proteins of the NM, particularly the INM, remain poorly defined due to the low abundance of these proteins in the cell and their generally insoluble character. The ability to isolate and characterize specific nuclear matrix proteins and the genetic sequences encoding them at the molecular level is anticipated to enhance the use of these proteins and their nucleic acids as marker molecules, and to enhance elucidation of the biological role of these proteins in vivo.

It is an object of this invention to provide genetic sequences encoding INM proteins useful as markers of malignant cell types. Another object is to provide enhanced means for identifying these proteins and their nucleic acids, including RNA transcripts, in samples. Yet another object of this invention is to provide compositions for use in diagnostic and other tissue evaluative procedures. Still another object is to provide genetic and amino acid sequences useful as target molecules in a cancer therapy. These and other objects and features of the invention will be apparent from the description, figures and claims which follow.

SUMMARY OF THE INVENTION

Molecular characterization data, including DNA sequence data, for two INM proteins now have been derived from an expression library, using monoclonal antibodies for these proteins. The proteins, designated herein as MT1 and MT2, are present at elevated levels in malignant tissue and extracellular fluids. Accordingly, the proteins and the genetic sequences encoding them are thought to be useful as marker molecules for identifying tissue tumor.genesis in cell or body fluid samples.

Full or partial clones of the genes encoding these proteins now have been isolated, and the DNA sequence, reading frames and encoded amino acid sequences of these DNAs determined. The DNA sequence for MT2 corresponds to the sequence disclosed by Yang, et al. (1992) *J. Cell. Biol.* 116:1303–1317, and Compton et al. (1992) *J. Cell. Biol.* 116:1395–1408, referred to therein as NuMA. The nucleic acid (and the encoded amino acid sequence) described herein for MT1 has not been described previously and also constitutes a novel sequence sharing little sequence homology with those sequences known in the art. In addition, MT1 has been subcloned into an expression vector, and the protein expressed as a cleavable fusion protein in *E. coli*. Both the MT1 and MT2 (NuMA) proteins are distributed throughout the nucleus (with the exception of the nucleolus) in non-mitotic cells, and localize to the spindle during mitosis, as determined immunofluoresence.

The genetic sequences described herein provide a family of proteins for each of the proteins MT1 and MT2, including allelic and species variants of MT1 and MT2. The family of proteins include these proteins produced by expression in a host cell from recombinant DNA, the DNA itself, and the host cells harboring and capable of expressing these nucleic acids. The recombinantly produced proteins may be isolated using standard methodologies such as affinity chromatography to yield substantially pure proteins. As used herein, "substantially pure" is understood to mean substantially free of undesired, contaminating proteinaceous material.

The family of proteins defined by MT1 includes proteins encoded by the nucleic acid sequence of Seq. ID No. 1, including analogs thereof. As used herein, "analog" is understood to include allelic and species variants, and other naturally-occurring and engineered mutants. Particularly envisioned are DNAs having a different preferred codon usage, those having "silent mutations" of the DNA of Seq. ID No.1, wherein the changes in the genetic sequence do not affect the encoded amino acid sequence, and DNAs encoding "conservative" amino acid changes, as defined by Dayoff et al., *Atlas of Protein Sequence and Structure;* vol. 5, Supp. 3, pp 345–362 (M. O. Dayoff, ed., Nat'l Biomed. Research Foundation, Washington, D.C. 1979.)

Accordingly, the nucleic acids encoding the protein family of MT1 may be defined as those sequences which hybridize to the DNA sequence of Seq. ID No.1 under stringent hybridization conditions. As used herein, stringent hybridization conditions are as defined in *Molecular Cloning: A Laboratory Manual,* Maniatis, et al. eds., Cold Spring Harbor Press, 1985, e.g.: hybridization in 50% formamide, 5× Denhardt's Solution, 5×SSPE, 0.1% SDS and 100 μg/ml denatured salmon sperm, and washing in 2×SSC, 0.1% SDS, at 37° C., and 1×SSC, 0.1% SDS at 68° C.

The family of proteins defined by MT2 includes proteins encoded by the nucleic acid sequence of Seq. ID No. 3, including analogs thereof, including allelic and species variants, and other naturally-occurring and engineered mutants. Particularly envisioned are DNAs having silent mutations, other preferred codon usages, and DNAs encoding conservative amino acid changes. The nucleic acids encoding the protein family of MT2 of this invention may be defined as those sequences which hybridize with the DNA sequence of Seq. ID No. 3 under stringent hybridization conditions.

In another aspect, the invention provides nucleic acid fragments ("oligonucleotides" or "oligomers") which hybridize to genetic sequences encoding MT1, but which do not necessarily encode functional proteins themselves. The oliognucleotides include probes for isolating genetic sequences encoding members of the MT1 family of proteins from a cDNA or genomic DNA library, and/or for identifying genetic sequences naturally associated with the MT1 protein coding sequence e.g., sequences lying upstream or downstream from the coding sequences. For example, where the nucleic acid fragment is to be used as a probe to identify other members of the MT1 family, the nucleic acid fragment may be a degenerate sequence as described in *Molecular Cloning: A Laboratory Manual,* Maniatis, et al. eds., Cold Spring Harbor Press, 1985, designed using the sequence of Seq. ID No.1 as a template. Accordingly, the oligonucleotide or nucleic acid fragment may comprise part or all of the DNA sequence of Seq. ID No. 1, or may be a biosynthetic sequence based on the DNA sequence of Seq. ID No. 1. The oligonucleotide preferably is suitably labelled using conventional labelling techniques.

The oligonucleotides also include sequences which hybridize with the mRNA transcript encoding the MT1 protein. These complementary sequences are referred to in the art and herein as antisense sequences. Antisense sequences may comprise part or all of the sequence of Seq. ID No. 1, or they may be biosynthetic sequences designed using the sequence of Seq. ID No. 1 as a template.

In still another aspect, the invention provides oligonucleotides which hybridize to the genetic sequences encoding members of the MT2 protein family. The fragments include antisense sequences and sequences useful as probes for identifying members of the MT2 family and/or for identifying associated noncoding sequences. The hybridizing nucleic acids may comprise part or all of the sequence of Seq. ID No. 3 or may be biosynthetic sequences designed using the DNA sequence of Seq. ID No. 3 as a template, preferably suitably labelled using conventional techniques.

The genetic sequences identified herein encode proteins identified as marker proteins indicative of a malignancy or other cellular dysfunction in a tissue. Thus, in another aspect, the invention provides compositions for obtaining antibodies useful for detecting cancer marker proteins in a sample using the proteins described herein in combination with a suitable adjuvant. In another aspect, the invention provides genetic templates for designing sequences which hybridize specifically with the mRNA transcripts encoding these proteins. In still another aspect, the invention provides isolated DNA sequences for use in expressing proteins and protein fragments for the design of binding proteins, including antibodies, which interact specifically with an epitope on MT1 or MT2. The invention also provides methods for evaluating the status of a tissue using the genetic sequences described herein, and the marker proteins encoded by them. Finally, the invention provides methods for treating a malignancy in an individual using these marker proteins, or the genetic sequences encoding them, as target molecules to inhibit or disable the cell's ability to undergo cell division.

BRIEF DESCRIPTIONS OF THE DRAWINGS

FIGS. 1A–1D is a schematic representation of the amino acid sequence of MT1 of Seq. ID No.1, showing:

FIG. 1A the location of the proline residues;

FIG. 1B the areas defined as α-helices within the sequence;

FIG. 1C the location of the cysteine residues; and

FIG. 1D the sites of cleavage by NTCB; and

FIGS. 2A–2B is a schematic representation of the amino acid sequence of MT2 of Seq. ID No.3, showing:

FIG. 2A the location of proline residues; and

FIG. 2B the areas defined as α-helices within the sequence.

DETAILED DESCRIPTION

In an attempt to characterize INM proteins useful as malignant cell markers in biological assays, the genetic sequences encoding two INM proteins, herein referred to as MT1 and MT2, now have been identified and characterized. DNA sequences encoding these proteins now have been cloned by probing expression libraries using monoclonal antibodies raised against the isolated INM proteins MT1 and MT2. The proteins were isolated from malignant cells essentially following the method of Penman and Fey, described in U.S. Pat. Nos. 4,882,268 and 4,885,236, the disclosures of which are herein incorporated by reference. The cloned DNAs, then were sequenced and their reading frames identified and analyzed. The genetic sequence encoding MT2 also has been disclosed by others (Yang, et al. (1992) *J. Cell. Biol.* 116:1303–1317 and Compton et al. (1992) *J. Cell. Biol.* 116:1395–1408), and is referred to by them as "NUMA". Comparison of MT1 and MT2 (NuMA)

with other sequences in the art indicate that the sequences encoding these proteins constitute sequences sharing little homology with previously described sequences.

MT1 also has been expressed as a cleavable fusion protein in *E. coli* and compared with the protein isolated from mammalian cells. Anti-MT1 antibodies raised against the natural-sourced MT1 protein also crossreact with the recombinantly produced protein. Both the natural-sourced and recombinantly produced proteins have the same apparent molecular weight when analyzed by SDS-PAGE (90 kD), equivalent pI values (5.4), and both proteins show the same cleavage pattern when cleaved with 2-nitro-3-thiocyanobenzoic acid (NTCB, see infra.)

Immunolocalization data on MT1 indicates that MT1 protein is distributed within the INM in non-mitotic cells as discrete punctate foci, nonuniformly distributed throughout the nucleoplasm of the INM. Specifically, the foci are present in the interchromatinic regions of the nucleus and are distributed in a stable association that remains after chromatin extraction, as is anticipated for an interior nuclear matrix protein. In addition, MT1 foci are excluded from the nucleolus and the nuclear lamina. Moreover, during mitosis, the distribution of MT1 changes and MT1 becomes aligned in a stellate or star-shaped pattern at the spindle of the dividing cell. The protein does not co-localize with the chromosomes, suggesting that MT1 may play a structural role during mitosis. The immunolocalization data is consistent with the MT1 amino acid sequence analysis data which fails to find structural homology with any known DNA binding motifs, such as the "leucine zipper."

While the MT2 (NuMA) protein has not yet been recombinantly expressed, the predicted molecular weight of 238 kDa for this protein, calculated from the predicted amino acid sequence (see Seq. ID No. 3), agrees with that of the natural-sourced material.

Immunolocalization studies on MT2 (NuMA) indicate that it also forms punctate foci located throughout the nucleoplasm of the non-mitotic cell, and also is excluded from the nucleolus. During mitosis the protein appears to migrate to the spindle poles of the dividing cell. The primary sequence appears to suggest a coiled-coil motif for the folded protein (Compton, et al. (1992) *J. Cell. Biol.* 116:1395–1408; Yang, et al. (1992) *J. Cell. Biol.* 116:1303–1317.)

I. How to Use

The nucleic acids disclosed herein encode proteins originally identified as marker proteins useful for identifying cell malignancies or other cell abnormalties. Specifically, significantly elevated levels of these proteins are detected in malignant cells and in extracellular fluids, e.g., sera, of cancer patients. (See PCT Publication WO93/09437, published May 13, 1991, the disclosure of which is incorporated herein by reference.) For example, the presence and/or abundance of these proteins or their transcripts in a sample containing cells or cell nuclear debris may be used to determine whether a given tissue comprises malignant cells or cells having other abnormalities, such as chromosomal abnormalities. The sample may be an exfoliated cell sample or a body fluid sample, e.g., a sample comprising blood, serum, plasma, urine, semen, vaginal secretions, spinal fluid, saliva, ascitic fluid, peritoneal fluid, sputum, tissue swabs, and body exudates such as breast exudate.

In addition, because INM proteins are released in soluble form from dying cells, the marker molecules may be used to evaluate the viability of a given tissue. For example, the marker proteins may be used to evaluate the status of a disease or the efficacy of a therapeutic treatment or procedure, by monitoring the release of these marker molecules into a body fluid over a period of time. Particularly useful body fluids include blood, serum, plasma, urine, semen, vaginal secretions, spinal fluid, saliva, ascitic fluid, peritoneal fluid, sputum, tissue swabs, and body exudates such as breast exudate. Methods for performing these assays are disclosed in U.S. Pat. Nos. 4,882,268 and 4,885,236 and in co-pending U.S. application Ser. No. 214,022, filed Jun. 30, 1988, now U.S. Pat. No. 5,273,877, and PCT Publication WO93/09437, published May 13, 1991, the disclosures of which are incorporated herein by reference.

All of these assays are characterized by the following general procedural steps:

1) detecting the presence and/or abundance of the marker protein or its transcript in "authentic" or reference samples;

2) detecting the presence and/or abundance of the marker protein or its transcript in the sample of interest; and 3) comparing the quantity of marker protein or its transcript in the sample of interest with the quantity present in the reference sample.

Where the assay is used to monitor tissue viability, the step of detecting the presence and abundance of the marker protein or its transcript in samples of interest is repeated at intervals and these values then are compared, the changes in the detected concentrations reflecting changes in the status of the tissue. Where the assay is used to evaluate the efficacy of a therapy, the monitoring steps occur following administration of the therapeutic agent or procedure (e.g., following administration of a chemotherapeutic agent or following radiation treatment.)

It is not required that the selected marker protein or transcript be totally unique, in the sense that the particular INM marker molecule is present in the target cell type and in no other. Rather, it is required that the marker molecule have a signal to noise ratio high enough to discriminate the preselected cell type in samples for which the assay is designed. For example, MT1 and MT2 proteins are useful as proteins indicating the presence of malignancy in cell samples because of their elevated expression levels in malignant cells, even though the proteins, or close analogs thereof, may be present commonly in nonmalignant cell types.

A brief description of general protein and nucleic acid assay considerations follows below. Details of particular assay conditions may be found in the assay references described above and incorporated herein by reference, and in published protocols well known in the art and readily available.

A. Protein Assays

Characterization of the MT1 and MT2 proteins at the molecular level as described herein allows one to characterize the proteins structurally and biochemically. Accordingly, following the disclosure of these genetic sequences and their encoded amino acid sequences, preferred binding epitopes may be identified which may be used to enhance assay conditions. For example, binding proteins may be designed which have enhanced affinity for the marker protein produced by particular cell types or as a function of particular malignancies. Similarly, binding proteins may be designed which bind preferentially to protein fragments released from dying cells. In addition, structural and/or sequence variations between proteins produced in normal and abnormal tissue now may be investigated and used to advantage. The genetic sequences may be manipulated as desired, e.g., truncated, mutagenized or the like, using standard recombinant DNA procedures known in the art, to obtained proteins having desired features useful for antibody production.

As will be appreciated by those skilled in the art, any means for specifically identifying and quantifying a marker protein of interest is contemplated. The currently preferred means for detecting a protein of interest in a sample is by means of a binding protein capable of interacting specifically with the marker protein. Labelled antibodies or the binding portions thereof in particular may be used to advantage. The antibodies may be monoclonal or polyclonal in origin, or may be biosynthetically produced. The amount of complexed marker protein, e.g., the amount of marker protein associated with the binding protein, then is determined using standard protein detection methodologies well described in the art.

A.1. Immunoassays

A variety of different forms of immunoassays currently exist, all of which may be adapted to detect and quantitate INM proteins and protein fragments. For exfoliated cell samples, as an example, the cells and surrounding fluid are collected and the INM proteins selectively isolated by the method of Penman and Fey, described in U.S. Pat. Nos. 4,882,268 and 4,885,236. These proteins then preferably are separated by two-dimensional gel electrophoresis and the presence of the marker protein detected by standard Western blot procedures.

For serum and other fluid assays where the marker proteins and/or protein fragments to be detected exist primarily in solution,, one of the currently most sensitive immunoassay formats is the sandwich technique. In this method, as described in PCT Publication WO93/09437, published May 13, 1993, two antibodies capable of binding the analyte of interest generally are used: e.g., one immobilized onto a solid support, and one free in solution, but labeled with some easily detectable chemical compound. Examples of chemical labels that may be used for the second antibody include radioisotopes, fluorescent compounds, and enzymes or other molecules which generate colored or electrochemically active products when exposed to a reactant or enzyme substrate. When samples containing the marker protein or protein fragment are placed in this system, the marker protein binds to both the immobilized antibody and the labelled antibody. The result is a "sandwich" immune complex on the support's surface. The complexed protein is detected by washing away nonbound sample components and excess labeled antibody, and measuring the amount of labeled antibody complexed to protein on the support's surface. The sandwich immunoassay is highly specific and very sensitive, provided that labels with good limits of detection are used. A detailed review of immunological assay design, theory and protocols can be found in numerous texts in the art, including *Practical Immunology*, Butt, W. R., ed., Marcel Dekker, New York, 1984.

In general, immunoassay design considerations include preparation of antibodies (e.g., monoclonal or polyclonal) having sufficiently high binding specificity for their antigen that the specifically-bound antibody-antigen complex can be distinguished reliably from nonspecific interactions. As used herein, "antibody" is understood to include other binding proteins having appropriate binding affinity and specificity for the marker protein. The higher the antibody binding specificity, the lower the antigen concentration that can be detected. Currently preferred binding specificity is such that the binding protein has a binding affinity for the marker protein of greater than about $10^5 M^{-1}$, preferably greater than about $10^7 M^{-1}$.

Antibody binding domains also may be produced biosynthetically and the amino acid sequence of the binding domain manipulated to enhance binding affinity with a preferred epitope. Identification of the genetic sequences for MT1 and MT2 can be used to advantage in the design and construction of preferred binding proteins. For example, a DNA encoding a preferred epitope may be recombinantly expressed and used to select an antibody which binds selectively to the epitope. The selected antibodies then are exposed to the sample under conditions sufficient to allow specific binding of the antibody to its specific nuclear matrix protein or protein fragment, and the amount of complex formed then detected. Specific antibody methodologies are well understood and described in the literature. A more detailed description of their preparation can be found, for example, in *Practical Immunology*, Butt, W. R., ed., Marcel Dekker, New York, 1984.

The choice of tagging label also will depend on the detection limitations desired. Enzyme assays (ELISAs) typically allow detection of a colored product formed by interaction of the enzyme-tagged complex with an enzyme substrate. Alternative labels include radioactive or fluorescent labels. The most sensitive label known to date is a chemiluminescent tag where interaction with a reactant results in the production of light. Useful labels include chemiluminescent molecules such as acridium esters or chemiluminescent enzymes where the reactant is an enzyme substrate. When, for example, acridium esters are reacted with an alkaline peroxide solution, an intense flash of light is emitted, allowing the limit of detection to be increased 100 to 10,000 times over those provided by other labels. In addition, the reaction is rapid. A detailed review of chemiluminescence and immunoassays can be found in Weeks, et al., (1983) *Methods in Enzymology* 133:366–387. Other considerations for fluid assays include the use of microtiter wells or column immunoassays. Column assays may be particularly advantageous where rapidly reacting labels, such as chemiluminescent labels, are used. The tagged complex can be eluted to a post-column detector which also contains the reactant or enzyme substrate, allowing the subsequent product formed to be detected immediately.

A.2. Antibody Production

The proteins described herein may be used to raise antibodies using standard immunological procedures well known and described in the art. See, for example, *Practical Immunology*, Butt, N. R., ed., Marchel Dekker, New York, 1984. Briefly, an isolated INM protein produced, for example, by recombinant DNA expression in a host cell, is used to raise antibodies in a xenogenic host. Preferred antibodies are antibodies that bind specifically to an epitope on the protein, preferably having a binding affinity greater than $10^5 M^{-1}$, most preferably having an affinity greater than $10^7 M^{-1}$ for that epitope. For example, where antibodies to a human INM protein, e.g. MT1 or MT2 is desired, a suitable antibody generating host is a mouse, goat, rabbit, guinea pig, or other mammal useful for generating antibodies. The protein is combined with a suitable adjuvant capable of enhancing antibody production in the host, and injected into the host, for example, by intraperitoneal administration. Any adjuvant suitable for stimulating the host's immune response may be used to advantage. A currently preferred adjuvant is Freund's complete adjuvant (an emulsion comprising killed and dried microbial cells, e.g., from Calbiochem Corp., San Diego, or Gibco, Grand Island, N.Y.). Where multiple antigen injections are desired, the subsequent injections comprise the antigen in combination with an incomplete adjuvant (e.g. cell-free emulsion).

Polyclonal antibodies may be isolated from the antibody-producing host by extracting serum containing antibodies to the protein of interest. Monoclonal antibodies may be produced by isolating host cells that produce the desired antibody, fusing these cells with myeloma cells using standard procedures known in the immunology art, and screening for hybrid cells (hybridomas) that react specifically with the INM protein and have the desired binding affinity.

Provided below is an exemplary protocol for monoclonal antibody production, which is currently preferred. Other protocols also are envisioned. Accordingly, the particular method of producing antibodies with the cancer marker protein compositions of this invention, is not envisioned to be an aspect of the invention. Also provided are representative assays demonstrating antibody specificity and protein quantification of antigen detected in cell culture supernatants and human sera.

Exemplary antibody production protocol: Balb/c by J mice (Jackson Laboratory, Bar Harbor, Me.) are injected intraperitoneally with purified INM protein (e.g., MT1) purified from the human cervical cell line CaSki, every 2 weeks for a total of 16 weeks. The mice are injected with a single boost 4 days prior to sacrifice and removal of the spleen. Freund's complete adjuvant (Gibco, Grand Island) is used in the first injection, incomplete Freund's in the second injection; subsequent injections are made with saline. Spleen cells (or lymph node cells) then are fused with a mouse myeloma line, e.g., using the method of Kohler and Milstein (1975) *Nature* 256:495, the disclosure of which is incorporated herein by reference, and using polyethylene glycol (PEG, Boehringer Mannheim, Germany). Hybridomas producing antibodies that react with nuclear matrix proteins then are cloned and grown as ascites. Hybridomas are screened by nuclear reactivity against the cell line that is the source of the immunogen, and by tissue immunochemistry using standard procedures known in the immunology art. Detailed descriptions of screening protocols, ascites production and immunoassays also are disclosed in WO93/09437, published May 13, 1993, incorporated hereinabove by reference.

Representative Assays

Table I below displays the binding results for assays performed with different antibodies raised against the two different cervical tumor cell line NM (nuclear matrix) antigen preparations (ME-180 and CaSKi, American Type Culture Collection, ATCC, Rockville, Md.). The 100-series antibodies are those raised against the ME-180 NM immunogen; the 300-series are those raised against CaSKi-NM immunogen.

method of Penman and Fey (Table II) and on cell culture supernatant from dying cells (Table III). The cell line T-47D (breast tumor cell line, ATCC, Rockville, Md.) was used as the source of antigen for both experiments and demonstrated that a dose response curve can be obtained with these assay conditions.

Table II shows the data generated using a standard ELISA immunoassay and purified NM, isolated by the method of Penman et al. Table III shows the data generated under the same conditions, but using the supernatant of dying cells as the antigen source. The cell line T-47D was used as the antigen source for both experiments and two antibodies, previously shown to have strong reactivity with the T-47D antigen by dot blot assay, were used (Ab 200-34, solid phase; Ab 200-4 as soluble antibody).

TABLE II

| Protein Concn. | OD | | |
|---|---|---|---|
| in NM prep. | rep 1 | rep 2 | mean |
| 10 mg/ml | 0.186 | 0.187 | |
| 1 mg/ml | 0.036 | 0.032 | 0.034 |
| 0.1 mg/ml | 0.021 | 0.009 | 0.015 |
| 0.0 | 0.000 | 0.003 | 0.001 |

TABLE III

| Concentration of supernatant | Mean OD | SD |
|---|---|---|
| Undiluted | 0.150 | 0.015 |
| 1:2 | 0.071 | 0.010 |
| 1:4 | 0.026 | 0.003 |
| 1:8 | 0.013 | 0.005 |
| No Sup | | |
| 2:1 | 0.401 | 0.015 |
| undiluted | 0.145 | 0.006 |
| 1:2 | 0.05 | 0.002 |
| 1:4 | 0.017 | 0.003 |
| 1:8 | 0.003 | 0.002 |
| No Sup | 0.000 | |

The data show that reliable dose response curves can be generated using these assay conditions to quantitate soluble NM antigen in solution. Following this protocol, other antibody combinations can be tested for their ability to detect and quantitate body fluid-soluble nuclear matrix proteins and protein fragments.

TABLE I

| | SOLUTIONS Ab | | | | | |
|---|---|---|---|---|---|---|
| CAPTURE Ab | 107-7 | 302-18 | 302-22 | 302-29 | 302-47 | 307-33 |
| 107-7 | NO RXN | NO RXN | NO RXN | RX | NO RXN | RXN |
| 302-18 | NO RXN | RXN | RXN | RXN | RXN | RXN |
| 302-22 | NO RXN | RXN | NO RXN | NO RXN | NO RXN | RXN |
| 302-29 | NO RXN | RXN | NO RXN | NO RXN | NO RXN | RXN |
| 302-47 | NO RXN | NO RXN | NO RXN | NO RXN | NO RXN | NO RXN |
| 307-33 | NO RXN | NO RXN | NO RXN | RXN | NO RXN | NO RXN |

As can be seen from the table, twelve of the thirty-six combinations tested result in a positive reaction. A positive reaction means that the two antibodies react with different epitopes on the same molecule. Only one antibody, 302-18, reacted in combination with itself.

Dose Response Assays

The first sandwich assay was obtained using antibodies 200-34 and 200-4 on nuclear matrix proteins isolated by the Dose response evaluation results of a 107.7/307.33 antibody combination is shown in Table IV, below, using ME-180 cell culture supernatant as the antigen source. The assay shows dose dependent detection of antigen in the tissue culture supernatant, demonstrating the ability of the assay to quantitate soluble interior nuclear matrix protein released from dying cells.

TABLE IV

| Antibody 107-7 solid phase, 307-33 soluble antibody, ME-180 supernatant. | | |
|---|---|---|
| Concentration of supernatant | Mean OD | SD |
| 3:1 | 0.906 | 0.009 |
| 3:2 | 0.456 | 0.011 |
| 3:4 | 0.216 | 0.007 |
| 3.8 | 0.099 | 0.005 |
| 3:16 | 0.052 | 0.002 |
| 3:32 | 0.031 | 0.005 |
| No Sup | | |

Next, interior nuclear matrix protein quantification was tested in supernatant from a variety of dying rumor tissues. Here, rumor and normal tissues were allowed to die in media as described supra. Supernatants were assayed in various configurations of sandwich assays. The results are shown in Table V, where all values are in units/gm, using ME-180 antigen as standard. As can be seen from Table V, antigen is released from each of the dying tissues, and the three assays are measuring different antigens. As expected, the increased cell death in tumor tissue is reflected in a higher average antigen value quantitated in cancer tissue versus normal tissue. In addition, significant differences in antigen quantities are seen in the different tissue sources, indicating that the soluble antigen quantities present in the supernatant vary in a cell-type specific manner.

Table VI shows the results of an analogous experiment performed using serum samples from cancer patients and normal blood donors. As for Table VI, ME-180 cell antigen was the standard. Results are reported in units/ml. A control experiment diluting supernatant antigen into serum and then quantitating the protein in solution indicates that serum has little or no effect on the assay. As can be seen in Table VI, like the results shown in Table V, serum samples from cancer patients reflect a higher rate of cell death as indicated by the quantifiably higher levels of antigen detected in these samples compared with those detected in the normal blood serum samples.

TABLE V

| | | ANTIBODY COMBINATIONS | |
|---|---|---|---|
| SAMPLE | SAMPLE # | 307-33 107-7 | 302-29 107-7 |
| NORMAL | 1 | 0.0 | 0.0 |
| NORMAL | 2 | 0.0 | 0.0 |
| NORMAL | 3 | 0.0 | 0.0 |
| NORMAL | 4 | 0.0 | 0.0 |
| NORMAL | 5 | 0.0 | 0.0 |
| NORMAL | 6 | 0.0 | 0.0 |
| NORMAL | 7 | 0.0 | 0.0 |
| NORMAL | 8 | 0.0 | 0.0 |
| NORMAL | 9 | 0.0 | 0.0 |
| NORMAL | 10 | 0.7 | 0.0 |
| NORMAL | 11 | 0.0 | 0.0 |
| NORMAL | 12 | 0.0 | 0.2 |
| NORMAL | 13 | 0.7 | 0.3 |
| NORMAL | 14 | 1.3 | 0.6 |
| NORMAL | 15 | 5.3 | 1.7 |
| NORMAL | 16 | 1.4 | 0.4 |
| NORMAL | 17 | 2.2 | 1.0 |
| NORMAL | 18 | 2.0 | 0.0 |
| NORMAL | 19 | 3.0 | 0.4 |
| NORMAL | 20 | 2.3 | 1.3 |
| NORMAL | 21 | 3.9 | 0.6 |
| NORMAL | 22 | 8.2 | 1.3 |
| NORMAL | 23 | 4.0 | 0.8 |
| NORMAL | 24 | 4.3 | 0.7 |
| NORMAL | 25 | 9.1 | 0.6 |
| NORMAL | 26 | 5.9 | 0.2 |
| NORMAL | 27 | 20.6 | 6.0 |
| NORMAL | 28 | 2.2 | 0.7 |
| NORMAL | 29 | 5.0 | 1.0 |
| NORMAL | 30 | 3.5 | 1.2 |
| NORMAL | 31 | 10.1 | 1.0 |
| NORMAL | 32 | 3.3 | 6.3 |
| NORMAL | 33 | 1.5 | 0.0 |
| NORMAL | 34 | 6.9 | 0.8 |
| NORMAL | 35 | 0.0 | 0.0 |
| NORMAL | 36 | 1.2 | 0.0 |
| BLADDER CA | 37 | 0.0 | 0.0 |
| BLADDER CA | 38 | 1.6 | 0.0 |
| BLADDER C | 39 | 0.0 | 0.0 |
| COLON CA | 40 | 8.9 | 7.0 |
| COLON CA | 41 | 28.4 | 24.3 |
| COLON CA | 42 | 28.6 | 17.9 |
| COLON CA | 43 | 11.6 | 8.1 |
| COLON CA | 44 | 12.8 | 6.8 |
| COLON CA | 45 | 6.4 | 0.9 |
| COLON CA | 46 | 3.7 | 2.4 |
| COLON CA | 47 | 28.3 | 27.3 |
| COLON CA | 48 | 17.5 | 20.2 |
| COLON CA | 49 | 4.7 | 0.0 |
| COLON CA | 50 | 11.7 | 10.3 |
| COLON CA | 52 | 5.7 | 0.0 |
| COLON CA | 53 | 5.1 | 0.5 |
| COLON CA | 54 | 6.0 | 1.8 |
| COLON CA | 55 | 13.1 | 2.3 |
| COLON CA | 56 | 9.6 | 5.8 |
| COLOREC CA | 57 | 58.2 | 41.3 |
| ENDOMETRIUM C | 58 | 10.3 | 6.8 |
| ENDOMETRIUM C | 59 | 4.7 | 1.9 |
| ENDOMETRIUM C | 60 | 9.4 | 7.1 |
| LUNG CA | 61 | 13.4 | 9.3 |
| LUNG CA | 62 | 11.9 | 7.9 |
| LUNG CA | 63 | 19.0 | 16.2 |
| LUNG CA | 64 | 16.7 | 7.8 |
| LUNG CA | 65 | 20.8 | 11.0 |
| OVARY CA | 66 | 21.1 | 16.9 |
| OVARY CA | 67 | 16.4 | 8.9 |
| OVARY CA | 68 | 11.6 | 8.3 |
| PROSTATE CA | 69 | 12.7 | 10.8 |
| PROSTATE CA | 70 | 4.9 | 2.8 |
| PROSTATE CA | 71 | 0.0 | 3.4 |
| PROSTATE CA | 72 | 15.4 | 7.0 |
| PROSTATE CA | 73 | 0.0 | 0.0 |

TABLE VI

| TISSUE TYPE | ASSAY 1* | ASSAY 2** |
|---|---|---|
| Breast normal 90-247 | NT# | 500 |
| Breast normal 90-252 | 7574 | 2705 |
| Breast normal 90-254 | NT | 1513 |
| Breast normal 90-264 | NT | 0 |
| Breast normal 90-268 | 139 | NT |
| Breast cancer 90-256 | 438 | NT |
| Breast cancer 90-275 | 2000 | NT |
| Breast cancer 90-287 | 20222 | 7333 |
| Cervix normal 90-279 | 2500 | NT |
| Cervical cancer 90-8083 | 12666 | NT |
| Colon normal 90-253 | 1009 | NT |
| Colon cancer 90-250 | 1450 | NT |
| Kidney normal 90-259 | 4250 | NT |
| Kidney cancer 90-289 | 2407 | NT |
| Liver normal | 2154 | 614 |
| Liver normal 90-451 | NT | 131 |

TABLE VI-continued

| TISSUE TYPE | ASSAY 1* | ASSAY 2** |
|---|---|---|
| Liver cancer | 2227 | 0 |
| Met liver 90-403 | NT | 300 |
| Lung normal 90-248 | 4391 | NT |
| Lung normal 90-246 | 4200 | NT |
| Lung normal 90-107 | NT | 4166 |
| Lung normal 90-118 | NT | 650 |
| Lung cancer 90-095 | NT | 5357 |
| Lung cancer 90-121 | NT | >12000 |
| Ovarian cancer | 8621 | 6517 |
| Ovarian cancer 90-260 | 6900 | NT |
| Ovarian cancer 90-291 | 2768 | NT |
| Ovarian cancer 90-291 | NT | 10909 |
| Uterine cancer 90-277 | 6574 | NT |
| Uterus normal 90-295 | 6574 | NT |
| average normal | 3447 | 1284 |
| average cancer | 9442 | 7069 |

*Assay 1 is 107.7 solid phase and 307.33 soluble phase.
**Assay 2 is 107.7 solid phase and 302.29 soluble phase.
NT means not tested.

B. Nucleic Acid Assays

The status of a tissue also may be determined by detecting the quantity of transcripts encoding these cancer marker proteins. The currently preferred means for detecting mRNA is by means of northern blot analysis using labeled oligonucleotides e.g., nucleic acid fragments capable of hybridizing specifically with the transcript of interest. The currently preferred oligonucleotide sequence is a sequence encoding a complementary sequence to that of at least part of the transcript marker sequence. These complementary sequences are known in the art as "antisense" sequences. The oligonucleotides may be oligoribonucleotides or oligodeoxyribonucleotides. In addition, oligonucleotides may be natural oligomers composed of the biologically significant nucleotides, i.e., A (adenine), dA (deoxyadenine), G (guanine), dG (deoxyguanine), C (cytosine), dC (deoxycytosine), T (thymine) and U (uracil), or modified oligonucleotide species, substituting, for example, a methyl group or a sulfur atom for a phosphate oxygen in the inter-nucleotide phosohodiester linkage. (see, for example, Section I.C, below.) Additionally, the nucleotides themselves, and/or the ribose moieties may be modified.

The sequences may be synthesized chemically, using any of the known chemical oligonucleotide synthesis methods well described in the art. For example, the oligonucleotides are advantageously prepared by using any of the commercially available, automated nucleic acid synthesizers. Alternatively, the oligonucleotides may be created by standard recombinant DNA techniques, by, for example, inducing transcription of the noncoding strand. For example, the DNA sequence encoding a marker protein may be inverted in a recombinant DNA system, e.g., inserted in reverse orientation downstream of a suitable promoter, such that the noncoding strand now is transcribed.

Useful hybridizing oligonucleotide sequences include any sequences capable of hybridizing specifically to the MT1 or MT2 primary transcripts. Accordingly, as will be appreciated by those skilled in the art, useful sequences contemplated include both sequences complementary to the DNA sequences provided in Seq. ID No. 1 (MT1) or Seq. ID No. 2 (MT2) which correspond to the protein coding regions, as well as sequences complementary to transcript sequences occurring further upstream or downstream from the coding sequence (e.g., sequences contained in, or extending into, the 5'- and 3' untranslated regions). Representative antisense sequences are described in Seq. ID Nos. 5 and 6. Seq. ID No. 5 describes a sequence complementary to the first 100 nucleotides of the MT1 protein coding sequence (compare Seq. ID Nos. 1 and 5) as well as the 53 nucleotide sequence occurring upstream of the initiation codon. The complementary nucleotides to the initiation codon occur at positions 298-300 in Seq. ID No. 5. Similarly, Seq. ID No. 6 describes a sequence complementary to the first 100 nucleotides of the MT2 protein coding sequence (compare Seq. ID Nos. 3 and 6), as well as the 48 nucleotide sequence occurring upstream of the initiation codon. The complementary nucleotides to the initiation codon occur at positions 298-300 in Seq. ID No. 6. Useful oligomers may be created based on part or all of the sequences in Seq. ID No. 5 and 6. However, as will be appreciated by those skilled in the art, other useful sequences which hybridize to other regions of the transcript readily are created based on the sequences presented in Seq. ID Nos. 1 and 3 and/or additional, untranslated sequences, such as are disclosed for MT2 (NuMA) in Compton et al. and Yang et al.

While any length oligonucleotide may be utilized to hybridize an mRNA transcript, sequences less than 8–15 nucleotides may be less specific in hybridizing to target mRNA. Accordingly, oligonucleotides typically within the range of 8–100 nucleotides, preferably within the range of 15–50, nucleotides are envisioned to be most useful in standard RNA hybridization assays.

The oligonucleotide selected for hybridizing to the INM transcript, whether synthesized chemically or by recombinant DNA, then is isolated and purified using standard techniques and then preferably labelled (e.g., with $^{35}$S or $^{32}$P) using standard labelling protocols.

A sample containing the marker transcript of interest then is run on an electrophoresis gel, the dispersed nucleic acids transferred to a nitrocellulose filter and the labelled oligonucleotide exposed to the filter under suitable hybridizing conditions, e.g. 50% formamide, 5×SSPE, 2×Denhardt's solution, 0.1% SDS at 42° C., as described in *Molecular Cloning: A Laboratory Manual*, Maniatis et al. Other useful procedures known in the art include solution hybridization, and dot and slot RNA hybridization. The amount of marker transcript present in a sample then is quantitated by measuring the radioactivity of hybridized fragments, using standard procedures known in the art.

Following a similar protocol, oligonucleotides also may be used to identify other sequences encoding members of the MT1 and MT2 protein families, for example, as described in the examples that follow. The methodology also may be used to identify genetic sequences associated with the protein coding sequences described herein, e.g., to identify noncoding sequences lying upstream or downstream of the protein coding sequence, and which may play a functional role in expression of these genes. Where new marker species are to be identified, degenerate sequences and/or sequences with preferred codon bias may be created, using the sequences of Seq. ID Nos. 1 or 3 as templates, and the general guidelines described in the art for incorporating degeneracies. (See, for example, *Molecular Cloning: A Laboratory Manual*, Maniatis, et al.)

C. Therapeutics

The proteins described herein are associated with the spindle apparatus during mitosis, and are present at elevated levels in malignant cells. Accordingly, without being limited to any particular theory, it is hypothesized that the proteins likely play a significant role in cell division, most likely a structurally related role. Accordingly, these proteins and their transcripts are good candidates as target molecules for a cancer chemotherapy.

C.1 Antisense Therapeutics

A particularly useful cancer therapeutic envisioned is an oligonucleotide complementary to part all of the marker transcript, capable of hybridizing specifically to the transcript and inhibiting translation of the mRNA when hybridized to the mRNA transcript. Antisense oligonucleotides have been used extensively to inhibit gene expression in normal and abnormal cells. See, for example, Stein et al. (1988) Cancer Res. 48:2659–2668, for a pertinent review of antisense theory and established protocols. Accordingly, the antisense nucleotides to MT1 and MT2 may be used as part of chemotherapy, alone or in combination with other therapies.

As described in Section I.B above, both oligoribonucleotide and oligodeoxyribonucleotide sequences will hybridize to an mRNA transcript and may be used to inhibit mRNA translation of the marker protein described herein. However, oligoribonucleotides generally are more susceptible to enzymatic attack by ribonucleases than deoxyribonucleotides. Hence, oligodeoxyribonucleotides are preferred for in vivo therapeutic use to inhibit mRNA translation in an individual.

Also, as described in Section I.B above, the therapeutically useful antisense oligonucleotides of the invention may be synthesized by any of the known chemical oligonucleotide synthesis methods well described in the art. Alternatively, a complementary sequence to part or all of the natural mRNA sequence may be generated using standard recombinant DNA technology. For example, the DNA encoding the protein coding sequence may be inserted in reverse orientation downstream of a promoter capable of expressing the sequence such that the noncoding strand is transcribed.

Since the complete nucleotide sequence of the protein coding sequence as well as additional 5' and 3' untranslated sequences are known for both MT1 and MT2 (see, for example, Seq. ID Nos. 1 and 3 and Compton et al.), and/or can be determined with this disclosure, antisense oligonucleotides hybridizable with any portion of the mRNA transcripts to these proteins may be prepared using conventional oligonucleotide synthesis methods known to those skilled in the art.

Oligonucleotides complementary to and hybridizable with any portion of the MT1 and MT2 mRNA transcripts are, in principle, effective for inhibiting translation of the transcript as described herein. For example, as described in U.S. Pat. No. 5,098,890, issued Mar. 24, 1992, the disclosure of which is incorporated herein by reference, oligonucleotides complementary to mRNA at or near the translation initiation codon site may be used to advantage to inhibit translation. Moreover, it has been suggested that sequences that are too distant in the 3' direction from the translation initiation site may be less effective in hybridizing the mRNA transcripts because of potential ribosomal "read-through", a phenomenon whereby the ribosome is postulated to unravel the antisense/sense duplex to permit translation of the message.

Representative antisense sequences for MT1 and MT2 transcripts are described in Seq. ID No. 5 (MT1) and Seq. ID No. 6 (MT2). The antisense sequences are complementary the sequence encoding the N-terminus of either the MT1 or MT2 marker protein, as well as part of the 5' untranslated sequences immediately upstream of the initiation codon. (See Section I.B, above for a detailed description of these sequences). As will be appreciated by those skilled in the art, antisense oligonucleotides complementary to other regions of the MT1 and/or MT2 transcripts are readily created using for example, the sequences presented in Seq. ID No. 1 and 3 as templates.

As described in Section I.B above, any length oligonucleotide may be utilized to hybridize to mRNA transcripts. However, very short sequences (e.g., less than 8–15 nucleotides) may bind with less specificity. Moreover, for in vivo use such short sequences may be particularly susceptible to enzymatic degradation. In addition, where oligonucleotides are to be provided directly to the cells, very long sequences may be less effective at inhibition because of decreased uptake by the target cell. Accordingly, where the oligonucleotide is to be provided directly to target cells, oligonucleotides having a length within the range of 8–50 nucleotides, preferably 15–30 nucleotides, are envisioned to be most advantageous.

An alternative means for providing antisense sequences to a target cell is as part of a gene therapy technique, e.g., as a DNA sequence, preferably part of a vector, and associated with a promoter capable of expressing the antisense sequence, preferably constitutively, inside the target cell. Recently, Oeller et al. ((1992) Science 254:437–539, the disclosure of which is in corporated by reference) described the in vivo inhibition of the ACC synthase enzyme using a constitutively expressible DNA sequence encoding an antisense sequence to the full length ACC synthase transcript. Accordingly, where the antisense sequences are provided to a target cell indirectly, e.g., as part of an expressable gene sequence to be expressed within the cell, longer oligonucleotide sequences, including sequences complementary to substantially all the protein coding sequence, may be used to advantage.

Finally, also as described in Section I.B, above, the therapeutically usefully oligonucleotides envisioned include not only native oligomers composed of naturally occurring nucleotides, but also those comprising modified nucleotides to, for example, improve stability and lipid solubility and thereby enhance cellular uptake. For example, it is known that enhanced lipid solubility and/or resistance to nuclease digestion results by substituting a methyl group or sulfur atom for a phosphate oxygen in the internucleotide phosphodiester linkage. Phosphorothioates ("S-oligonucleotides" wherein a phosphate oxygen is replaced by a sulfur atom), in particular, are stable to nuclease cleavage, are soluble in lipids, and are preferred, particularly for direct oligonucleotide administration. S-oligonucleotides may be synthesized chemically by the known automated synthesis methods described in Section I.B, above.

Suitable oligonucleotide sequences for mRNA translation inhibition are readily evaluated by a standard in vitro assay using standard procedures described herein and well characterized in the art. An exemplary protocol is described below, but others are envisioned and may be used to advantage.

A candidate antisense sequence is prepared as provided herein, using standard chemical techniques. For example, an MT1 antisense sequence may be prepared having the sequence described by positions 285–315 of Sequence ID No. 5 using an Applied Biosystems automated DNA Synthesizer, and the oligonucleotide purified accordingly to manufacturer's instructions. The oligonucleotide then is provided to a suitable malignant cell line in culture, e.g., ME-180, under standard culture conditions, to be taken up by the proliferating cells.

Preferably, a range of doses is used to determine effective concentrations for inhibition as well as specificity of hybridization. For example, a dose range of 0–100 μg oligonucleotide/ml may be assayed. Further, the oligonucleotides may be provided to the cells in a single transfection, or as part of a series of transfections.

Antisense efficacy may be determined by assaying a change in cell proliferation over time following transfection, using standard cell counting methodology and/or by assaying for reduced expression of marker protein, e.g., by immunofluorescence, as described in Section I.A, above. Alternatively, the ability of cells to take up and use thymidine is another standard means of assaying for cell division and maybe used here, e.g., using $^3$H thymidine. Effective antisense inhibition should inhibit cell division sufficiently to reduce thymidine uptake, inhibit cell proliferation, and/or reduce detectable levels of marker proteins.

Useful concentration ranged are envisioned to vary according to the nature and extent of the neoplasm, the particular oligonucleotide utilized, the relative sensitivity of the neoplasm to the oligonucleotides, and other factors. Useful ranges for a given cell type and oligonucleotide may be determined by performing a standard dose range experiment as described here. Dose range experiments also may be performed to assess toxicity levels for normal and malignant cells. Concentrations from about 1 to 100 μg/ml per $10^5$ cells may be employed to advantage.

For in vivo use, the antisense oligonucleotides may be combined with a pharmaceutical carrier, such as a suitable liquid vehicle or excipient and an optional auxiliary additive or additives. The liquid vehicles and excipients are conventional and commercially available. Illustrative thereof are distilled water, physiological saline, aqueous solutions of dextrose, and the like. For in vivo cancer therapies, the antisense sequences preferably are provided directly to the malignant cells, as by injection to the neoplasm locus. Alternatively, the oligonucletide may be administered systemically, provided that the antisense sequence is associated with means for directing the sequences to the target malignant cells.

In addition to administration with conventional carriers, the antisense oligonucleotides may be administered by a variety of specialized oligonucleotide delivery techniques. For example, oligonucleotides maybe encapsulated in liposomes, as described in Maniatis et al., Mannino et al. (1988) *BioTechnology* 6:682, and Felgner et al. (1989) *Bethesda Res. Lab. Focus* 11:21. Reconstituted virus envelopes also have been successfully used to deliver RNA and DNA to cells. (see, for example, Arad et. al., (1986) *Biochem. Biophy. Acta.* 859, 88–94.)

For therapeutic use in vivo, the antisense oligonucleotides are provided in a therapeutically effective amount, e.g., an amount sufficient to inhibit target protein expression in malignant cells. The actual dosage administered may take into account whether the nature of the treatment is prophylactic or therapeutic in nature, the age, weight, health and sex of the patient, the route of administration, the size and nature of the malignancy, as well as other factors. The daily dosage may range from about 0.01 to 1,000 mg per day. Greater or lesser amounts of oligonucleotide may be administered, as required. As will be appreciated by those skilled in the medical art, particularly the chemotherapeutic art, appropriate dose ranges for in vivo administration would be routine experimentation for a clinician. As a preliminary guideline, effective concentrations for in vitro inhibition of the target molecule may be determined first, as described above.

II.B PROTEIN INHIBITION

In another embodiment, the cancer marker protein itself may be used as a target molecule. For example, a binding protein designed to bind the marker protein essentially irreversibly can be provided to the malignant cells e.g., by association with a ligand specific for the cell and known to be absorbed by the cell. Means for targeting molecules to particular cells and cell types are well described in the chemotherapeutic art.

Binding proteins maybe obtained and tested as described in Section I.A above. For example, the binding portions of antibodies maybe used to advantage. Particularly useful are binding proteins identified with high affinity for the target protein, e.g., greater than about $10^9 M^{-1}$. Alternatively, the DNA encoding the binding protein may be provided to the target cell as part of an expressable gene to be expressed within the cell following the procedures used for gene therapy protocols well described in the art. (see, for example, U.S. Pat. No. 4,497,796, and *Gene Transfer*, Vijay R. Baichwal, ed., (1986). It is anticipated that the complexed INM protein will be disabled and can inhibit cell division thereby.

AS described above for antisense nucleotides, for in vivo use, suitable binding proteins may be combined with a suitable pharmaceutical carrier, such as physiological saline or other useful carriers well characterized in the medical art. The parmaceutical compositions may be provided directly to malignant cells, e.g., by direct injection, or may be provided systemically, provided the binding protein is associated with means for targeting the protein to target cells. Finally, suitable dose ranges and cell toxicity levels may be assessed using standard dose range experiments. Therapeutically effective concentrations may range from 0.1–1,000 mg per day. As described above, actual dosages administered may vary depending, for example, on the nature of the malignanacy, the age, weight and health of the individual, as well as other factors.

II. EXEMPLIFICATION

The following examples further describe how the genetic sequences encoding MT1 and MT2 proteins were isolated and characterized, including the current best mode for their cloning and characterization, without limiting the scope thereof. For example, INM protein expression in *E. coli* is described herein. However, other prokayrotic and eukaryotic cell expression systems also are contemplated for recombinant expression of the proteins described herein. Other useful hosts contemplated include Saccharomyces, the insect/baculovirus expression system, and mammalian cells such as xenogenic myeloma cells and the well-characterized chinese hamster ovary cell lines.

MT1

As described in co-pending application Ser. No. 785,804, MT1 expression levels are enhanced significantly in carcinoma cells as determined by body fluid assays performed on cultured cervical tumor cell lines (Me-180 and CaSki, ATCC, Rockville, Md).

The natural-sourced MT1 protein first was separated from human cervical tumor cells essentially following the procedure of Penman and Fey described in U.S. Pat. Nos. 4,882,268 and 4,885,236. Cells from the human cervical tumor cell lines CaSki and ME180 (obtained from the American Tissue Culture Collection, ATCC, Rockville, Md.) were grown to confluence and removed from flasks by trypsinization. Suspended cells were washed twice with phosphate buffered saline (PBS) and extracted with cytoskeletal buffer (CSK): 100 mM NaCl, 300 mM sucrose, 10 mM PIPES, 3 mM $MgCl_2$, 1 mM EGTA, 0.5% Triton X-100, 1.2 mM PMSF for 1 min at 4° C., followed by extraction in cold RSB (reticulocyte suspension buffer)/double detergent buffer: 100 mM NaCl, 3 mM $MgCl_2$, 10 mM Tris, pH 7.4, 1% Tween 40, 0.5% deoxycholate, 1.2 mM PMSF. Alternatively, cells were extracted twice with the RBS/double detergent buffer. The two extraction protocols produced very similar preparations. The extracted cells were digested for 30 min at room temperature in digestion buffer: 50 mM NaCl, 300 mM sucrose, 0.5% Triton X-100, 10 mM PIPES (pH 6.8), 3 mM MgCl$_2$, 1 mM EGTA, 1.2 mM PMSF, containing 100 μg of both RNase A and DNase I. Chromatin was extracted from the digested nuclei by the addition of 2M ammonium sulfate to a final concentration of 0.25M. The extracted nuclear matrix-intermediate filament (NM-IF) scaffolds then were sedimented at 3700×g for 15 min.

The resulting pellet then was resuspended in disassembly buffer: 8M urea, 20 mM MES (pH 6.6), 1 mM EGTA, 1.2 mM PMSF, 0.1 mM MgCl$_2$, 1% 2-mercaptoethanol, and the pellet sonicated and dialyzed overnight with 3 changes of 2000 volumes of assembly buffer: 0.15M KCl, 25 mM imidazole (pH 7.1), 5 mM MgCl$_2$, 2 mM DTT, 0.125 mM EGTA, 0.2 mM PMSF. The dialysate then was centrifuged at 100×g for 1 h and the NM proteins recovered from the supernatant. Alternatively, NM-IF scaffolds were extracted directly with E400 buffer: 0.4M NaCl, 0.02M Tris pH 7.5, 0.1 mM MCl$_2$, 0.5% 2-mercaptoethanol, 1.2 mM PMSF, for 30 min at 4° C., as described by von Kries et al. (1991) *Cell* 64:123–135. The intermediate filament-rich pellet then was removed after centrifugation for 90 min at 40K rpm in a Beckman 70.1 Ti rotor. The supernatant remaining is enriched in MT1 protein with little cytokeratin contamination.

MT1-specific antibodies were produced by standard procedures. Specifically, Balb/c by J mice (Jackson Laboratory, Bar Harbor, Me.) were injected intraperitoneally with purified Caski NM protein every 2 weeks for a total of 16 weeks. The mice were injected with a single boost 4 days prior to sacrifice and removal of the spleen. Freund's complete adjuvant was used in the first injection, incomplete Freund's in the second injection; subsequent injections were made with saline. Spleen cells were fused with the SP2/O-Ag14 mouse myeloma line (ATCC, Rockville, Md.) using the standard fusion methodologies well known in the art. Hybridomas producing antibodies that reacted with nuclear matrix proteins were cloned and grown as ascites. MT1 specificity was assessed both by immunoflourescence spectroscopy and Western blot analysis.

The cDNA clones for MT1 were obtained from a Lambda ZAP expression library (Stratagene, La Jolla, Calif.). Library screening was carried out according to the manufacturer's instructions. Briefly, a single positive clone containing a 2.45 kb insert was identified and subcloned into pBluescript II vectors (Stratagene, La Jolla, Calif.) opened at the EcoRI and XhoI cloning sites. The resulting plasmid, pMT1, was sequenced directly and further subcloned to produce the MT1 fusion protein (see below).

The cDNA sequences were obtained using the standard dideoxy method described in the art. Double stranded sequencing was done utilizing the pMT1 vector primed with appropriate primers according to manufacturer's instructions (Stratagene, La Jolla, Calif.). Internal sequences were obtained using synthetic primers, created based on the identified sequence.

The entire nucleotide sequence and predicted amino acid sequence for MT1 are shown in Seq. ID No. 1. The cDNA clone retains a polyadenylation signal a putative initiation codon, a continuous open reading frame and codon utilization consistent with a human gene. The predicted amino acid sequence of MT1 consists of 639 amino acids encoding a protein of 70.5 kD with a pI of 5.47. The primary structure, as predicted by the Chou-Fasman algorithm (Chou and Fasman, (1978) *Adv. Enzymol. Relat. Areas Mol. Biol.* 47:145–148), consists of 72% alpha helix of which 56% is extended helix.

The primary structure of MT1, represented in FIG. 1, contains 27 proline residues which generally occur in pairs or triplets throughout the molecule. The proline distribution within the sequence is illustrated in FIG. 1A, where diamonds represent the proline residues. Proline pairs and triplets are indicted by stacked diamonds. At the N terminus, a 40 amino acid stretch contains a cluster of 8 prolines (residues 42–81, Seq. ID No. 1) that occur as pairs separated by 3 or fewer amino acids. A similar proline-rich region occurs in the C terminus of MT1 (residues 551–563) where 6 prolines occur in a 13 amino acid stretch. Both proline-rich regions likely lie on the protein surface, based on probability calculations determined by the technique of Emini et al. (1985) *J. Virol.* 55:836–839. The high proline density also may explain the anomalous apparent molecular weight of the protein as determined by SDS polyacrylamide gel electrophoresis. As described above, the predicted molecular weight for MT1, calculated from the amino acid sequence, is 70.1 kD. However, as described below, both the natural-sourced and recombinant protein migrate as a 90 kD protein on an SDS polyacrylamide gel. Alternatively, it is also possible that the molecular weight variation may result from some post-translational modification achievable in both prokaryotic and eukaryotic cells.

Between the two proline-rich termini, MT1 displays a sequence consistent with a region of extended alpha helix structure, indicated by the hatched structure in FIG. 1B. The extended helix is interrupted in 4 places by short helix-distorting amino acidustretches that usually include a pair of proline residues. A preliminary hypothesis as to the structure of MT1 based on these theoretical calculations is that the molecule consists of an extended rod that is bounded on either end by a globular, proline-rich domain.

Analysis of all available sequence databases indicates that MT1 has a novel sequence that bears no significant homology to any known protein. In addition, the sequence appears to lack any known, identifiable DNA binding motif such as the leucine zipper motif.

The cloned MT1 DNA was used to perform standard Northern blot analysis of total and poly A+ RNA from ME180 cells, using standard procedures and 15 μg RNA. After blotting and hybridization with $^{32}$P-labelled pMT1 DNA, a single mRNA band was detected in the poly A+ fraction. This band was not apparent in the total RNA lane after a 48 h exposure of the autoradiogram, indicating that the MT1 message is a low abundance species. Northern blot analysis indicates that the MT1 protein is translated from a single mRNA. Northern blot analysis also indicates that the MT1 RNA includes approximately 500 bp 5' of the protein-coding sequence presented in Seq. ID No. 1. This upstream sequence may represent one or more untranslated sequences and/or may encode additional protein coding sequences.

A fusion protein for MT1 was obtained using the insert from the pMT1 construct described above and in Seq. ID No. 1, and the pMAL expression system (New England Biolabs Inc., Beverly, Mass.). In this system the gene of interest (MT1) is cloned into the pMal-c vector (New England Biolabs Inc., Beverly, Mass.) and the vector transfected into *E. coli* and expressed to produce a fusion protein containing both the protein of interest and the maltose binding protein. The maltose binding protein allows the fusion protein to be selectively purified in the presence of maltose and can be subsequently cleaved by proteolytic clavage with Factor Xa to yield intact, recombinant MT1 protein. Here, MT1 cDNA was cloned into the pMAL-c vector such that the initiation AUG codon was directly continuous with the 5' terminus of the maltose binding protein. After proteolytic cleavage with factor Xa the resulting MT1 fusion protein retains the complete amino acid sequence encoded by the MT1 cDNA with no additional amino acids. All experimental details of the pMAL system were carried out according to the manufacturer's instructions.

As described above, both the natural-sourced and recombinantly produced protein have an electrophoretic mobility consistent with an apparent molecular weight of about 90 kD on SDS-PAGE. In addition, the pI of both proteins is equivalent (5.4) and consistent with the predicted pI as calculated from the amino acid sequence. Peptide mapping of both proteins by cleavage at cysteine residues with 2-nitro-5-thiocyanobenzoic acid (NTCB), following the method of Leto and Marchesi (1984) *J. Biol. Chem.* 259:4603–4049, yields equivalent peptide fragments which share the same MT1 cross reactivity by Western blot analysis. Moreover, the number and size of the peptide fragments produced are consistent with those predicted from the proposed MT1 amino acid sequence.

MT2

Like MT1, MT2 expression levels are enhanced significantly in malignant cells, as determined by serum assays.

Following the same general procedure as for MT1, a composition selectively enriched for MT2 was obtained from ME-180 cells (cervical carcinoma cells, from ATCC, Rockville, Md.), and MT2-specific antibodies prepared. These antibodies then were used to obtained a partial cDNA clone for MT2, by screening a lambda ZAP expression library, as for MT-1. The partial clone retrieved then was subcloned into a pBluescript II vector (pMT2) and the MT2 cDNA sequenced using standard techniques. The sequenced DNA, which corresponds to residues 1366 to 2865 of Seq. ID No. 3, then was analyzed to determine the reading frame and encoded amino acid sequence. The complete coding sequence subsequently was determined and is presented in Seq. ID No. 3. (Compton et al. (1992) *J. Cell. Biol.* 116:1395–1408). The nucleotide sequence and predicted amino acid sequence for MT2 are described in Seq. ID No. 3.

The primary structure of MT2 is represented schematically in FIG. 2: The protein appears to comprise at least 6 helical regions separated by proline pairs, (See FIGS. 2A and B.) The primary structure may allow the protein to form a coiled-coil structure in solution. As for FIG. 1, prolines are indicated by diamonds and helices by hatched boxes. In addition, both the N and C termini of MT2 appear to fold as globular domains (Compton et al. (1992) *J. Cell Biol.* 116: 1395–1408.)

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An isolated nucleic acid comprising the DNA sequence of Seq. ID No. 1, or a nucleic acid sequence variant thereof, wherein said variant is characterized as
   (a) being a nucleic acid sequence that hybridizes under stringent hybridization conditions with a nucleic acid sequence complementary to the DNA of Seq. ID No. 1, and
   (b) encoding an epitope which specifically binds an immunoglobulin that specifically binds the amino acid sequence encoded by the DNA of Seq. ID No. 1.

2. The isolated nucleic acid of claim 1, comprising nucleotides 94 through 2010 of Seq. ID. No. 1.

3. A host cell transfected with the nucleic acid of claim 1 or 2.

4. A vector comprising the nucleic acid of claim 1 or 2.

5. An isolated nucleic acid comprising the DNA sequence of Seq. ID No. 3, or a nucleic acid sequence variant thereof, wherein said variant is characterized as
   (a) being a nucleic acid sequence that hybridizes under stringent hybridization conditions with a nucleic acid sequence complementary to the DNA of Seq. ID No. 3, and
   (b) encoding an epitope which specifically binds an immunoglobulin that specifically binds the amino acid sequence encoded by the DNA of Seq. ID No. 3.

6. The isolated nucleic acid of claim 5, comprising nucleotides 1366 through 2865 of Seq. ID No. 3.

7. The isolated nucleic acid of claim 5, comprising nucleotides 1 through 6303 of Seq. ID No. 3.

8. A host cell transfected with the nucleic acid of claim 5, 6 or 7.

9. A vector comprising the nucleic acid of claim 5, 6 or 7.

* * * * *